(12) United States Patent
DeMello et al.

(10) Patent No.: US 6,846,818 B2
(45) Date of Patent: Jan. 25, 2005

(54) SELECTIVE INHIBITORS OF CYCLOOXYGENASE-2

(75) Inventors: Kristin Lundy DeMello, Ledyard, CT (US); Brian S. Bronk, Gales Ferry, CT (US); Rhonda Marie Crosson, Ann Arbor, MI (US)

(73) Assignee: Pfizer Inc., New York, NY (US)

( * ) Notice: Subject to any disclaimer, the term of this patent is extended or adjusted under 35 U.S.C. 154(b) by 6 days.

(21) Appl. No.: 10/414,856

(22) Filed: Apr. 16, 2003

(65) Prior Publication Data

US 2003/0207897 A1 Nov. 6, 2003

Related U.S. Application Data

(60) Provisional application No. 60/374,372, filed on Apr. 22, 2002.

(51) Int. Cl.[7] .................. C07D 401/12; C07D 403/12; C07D 403/14; A61K 31/541; A61K 31/5355

(52) U.S. Cl. .................. 514/228.2; 514/235.2; 514/241; 514/252.06; 514/254.09; 514/256; 514/255.05; 514/323; 514/339; 514/414; 544/62; 544/144; 544/238; 544/333; 544/373; 544/405; 544/215; 546/208; 546/277.2; 548/468

(58) Field of Search .................. 544/62, 144, 238, 544/333, 373, 405, 215; 546/208, 277.7; 548/468; 514/228.2, 235.2, 241, 252.06, 254.09, 255.05, 256, 323, 339, 414

(56) References Cited

U.S. PATENT DOCUMENTS

| | | | |
|---|---|---|---|
| 3,882,236 A | 5/1975 | Molloy | 424/274 |
| 4,006,161 A | 2/1977 | Holmes et al. | 260/325 R |
| 4,160,032 A | 7/1979 | Hardtmann | 424/274 |
| 4,569,942 A | 2/1986 | Kadin | 514/414 |
| 5,344,991 A | 9/1994 | Reitz et al. | 568/34 |
| 5,380,738 A | 1/1995 | Norman et al. | 514/374 |
| 5,434,178 A | 7/1995 | Talley et al. | 514/406 |
| 5,466,823 A | 11/1995 | Talley et al. | 548/377.1 |
| 5,474,995 A | 12/1995 | Ducharme et al. | 514/241 |
| 5,510,368 A | 4/1996 | Lau et al. | 514/419 |
| 5,521,207 A | 5/1996 | Graneto | 514/406 |
| 5,604,260 A | 2/1997 | Guay et al. | 514/605 |
| 5,968,969 A | 10/1999 | Ahmed | 514/414 |
| 6,048,850 A | 4/2000 | Young et al. | 514/183 |

FOREIGN PATENT DOCUMENTS

| | | | |
|---|---|---|---|
| EP | 0393936 A | 10/1990 | ......... C07D/209/34 |
| EP | 0 826 685 A1 | 8/1997 | |

OTHER PUBLICATIONS

Vane, et al., "Inducible isoforms of cyclooxygenase and nitric–oxide synthase in inflammation", *Proc. Natl. Acad. Sci* 91, pp. 2046–2050 (1994).

Gassman, et al., "Substituent Effects on the Carbon–13 Spectra of Oxindoles", *J. Org. Chem.* 42(8), pp. 1340–1344 (1977).

Beckett, et al., "Substituted Osindoles–1 The Preparation and Spectral Chacteristics of some Simple Oxindole Derivatives", *Tetrahedron* 24, pp. 6093–6109 (1968).

McEvoy, et al., "Borane Reduction of 3–Substituted 2–Indolinones", *J. Org. Chem.* 38(19), pp. 3350–3352 (1973).

Simet, "The Preparation of 6–Trifluoromethylisatin", *Notes* 28, pp. 3580–3581 (1963).

Wright, et al., "Cyclic Hydroxamic Acids Derived from Indole", *Journal of the American Chemical Society* 78, pp. 221–224 (1956).

Walker, "Synthesis of 5,6–Dimethoxyindoles and 5,6–Dimethoxyoxindoles. A New Synthesis of Indoles", *Journal of the American Chemical Society* 77, pp. 3844–3850 (1955).

Moore, et al. "Tenidap, a structurally novel drug for the treatment of arthritis; Antiinflammatory and analgesic properties", *Inflamm. Res.* 45, pp. 54–61 (1996).

Brideau, et al. "A human whole blood assay for clinical evaluation of biochemical efficacy of cyclooxygenase inhibitors", *Inflamm. Res.* 45, pp. 68–74 (1996).

Wieland, et al. "Synthese einiger Methoxy–oxindole and –indole", *Chemische Berichte* 96, pp. 253–259 (1963).

Ricketts, et al., "Evaluation of selective inhibition of canine cyclooxygenase 1 and 2 by carprofen and other nonsteroidal anti–inflammatory drugs", *AJVR* 59(11), pp. 1441–1446 (1998).

Cashin, et al., "The pharmacology of benoxaprofen (2–[4–chlorophenyl]–α–methyl–5–benzoxazole acetice acid), LRCL 3794, a new compound with anti–inflammatory activity apparently unrelated to inhibition of prostaglandin synthesis", *J. Pharm. Pharmac.* 29, pp. 330–336 (1977).

(List continued on next page.)

Primary Examiner—Mukund J. Shah
Assistant Examiner—Kahsay Habte
(74) Attorney, Agent, or Firm—Peter C. Richardson; Thomas A. Wootton; Mary J. Hosley

(57) ABSTRACT

The present invention relates to cyclooxygenase-2 (COX-2) selective inhibitors of formula I:

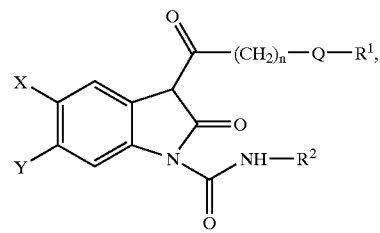

pharmaceutical compositions containing them, to their medicinal use, and to their preparations. The compounds of the invention are particularly useful in the treatment or alleviation of inflammation and inflammation associated disorders, such as, for example, rheumatoid arthritis and osteoarthritis, and in the relief of pain, such as, for example, pain associated with surgery or trauma, in mammals, preferably felines and canines.

25 Claims, No Drawings

OTHER PUBLICATIONS

Lombardino, et al., "Acidic Antiinflammatory Agents—Correlations of Some Physical, Pharmacological and Clinical Data", *Arzneim.–Forsch (Drug. Res.)* 25(10), pp. 1629–1635 (1975).

Ezer, et al., "Antagonism of the gastrointestinal ulcerogenic effect of some non–steroidal anti–inflammatory agents by sodium salicylate", *J. Pharm. Pharmac.* 28, pp. 655–656 (1976).

Winter, et al., "Carrgeenin–Induced Edema In Hind Paw of the Rat as an Assay for Antiiflammatory Drugs", *Proc. Soc. Exp. Biol. Med.* 111, pp. 544–547 (1962).

Protiva, et al., "Potential Metabolites of Tricyclic Neuroleptics and their Fluorinated Analogues; 3–Hydrox–, 3–Methoxy–and 3–Fluoro–10–(4–Methylopiperazino)–10, 11–Dihydrodibenzo[b,f]Thiepin", *Collection Czechoslov. Chem Commun.* 44, pp. 2108–2123 (1979).

Sandler, et al., "Isocyanates", *Organic Functional Group Preparations* 1, pp. 364–369 (1983).

Coffey, *Rodd's Chemistry of Carbon Compounds* 4 (Part A), pp. 448–450 (1973).

SELECTIVE INHIBITORS OF CYCLOOXYGENASE-2

CROSS-REFERENCE TO RELATED APPLICATION

This application claims priority from U.S. provisional application No. 60/374,372 filed on Apr. 22, 2002.

FIELD OF THE INVENTION

The present invention relates to compounds that selectively inhibit cyclooxygenase-2 (COX-2), an enzyme involved in the synthesis of prostaglandins. The compounds of the present invention are particularly useful in the treatment or alleviation of inflammation and inflammation associated disorders, such as, for example, rheumatoid arthritis and osteoarthritis, and in the relief of pain, such as, for example, pain associated with surgery or trauma. Compositions containing the selective COX-2 inhibitors also are provided, as well as methods for administering the compounds and compositions to patients in need thereof.

BACKGROUND OF THE INVENTION

Two forms of cyclooxygenases are now known, a constitutive isoform (COX-1) and an inducible isoform (COX-2) of which expression is upregulated at sites of inflammation (Vane, J. R.; Mitchell, et. al., *Proc. Natl. Acad. Sci. USA*, 1994, 91, 2046). COX-1 appears to play a physiological role and to be responsible for gastrointestinal and renal protection. On the other hand, COX-2 appears to play a pathological role and is believed to be the predominant isoform present in inflammation conditions. The therapeutic use of conventional COX inhibitors are limited due to drug associated side effects, including life threatening ulceration and renal toxicity. Compounds that selectively inhibit COX-2 would exert anti-inflammatory effects without the adverse side effects associated with COX-1 inhibition.

A number of selective COX-2 inhibitors have been described which are anti-inflammatory in a variety of animal models but which, unlike non-selective COX inhibitors, do not produce gastrointestinal pathology. See, for example, U.S. Pat. Nos. 5,380,738; 5,344,991; 5,434,178; 5,466,823; 5,474,995; 5,510,368; 5,521,207; 5,604,260; and 6,048,850, all of which are incorporated herein by reference.

Kadin, U.S. Pat. No. 4,569,942 ("Kadin"), incorporated herein by reference, discloses a broad class of N,3-disubstituted 2-oxindole-1-carboxamide compounds that are generically referred to as inhibitors of cyclooxygenase and lipoxygenase, and that are said to be useful as analgesic and antiinflammatory agents in mammalian subjects, particularly man. Kadin, however, does not mention inhibition of COX-2 and, therefore, does not identify or suggest which compounds within the broad disclosure might have a particular utility for inhibiting COX-2, much less in animals other than humans.

SUMMARY OF THE INVENTION

The present invention provides compounds that selectively inhibit cyclooxygenase-2 ("COX-2"), an enzyme involved in the synthesis of prostaglandins. These compounds are particularly useful in the treatment or alleviation of inflammation and inflammation associated disorders, such as, for example, rheumatoid arthritis and osteoarthritis, and in the relief of pain, such as, for example, pain associated with surgery or trauma and pain associated with the aforementioned inflammatory disorders.

Accordingly, in one embodiment, the present invention provides compounds of the following formula I:

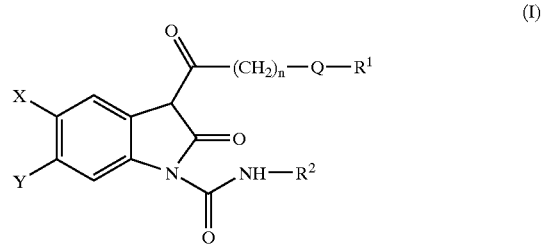

or the pharmaceutically-acceptable salts thereof;

wherein X is hydrogen, halogen, $-NO_2$, $(C_1-C_6)$alkyl, $-CF_3$, $(C_3-C_8)$cycloalkyl, $(C_1-C_6)$alkyl-O—, $(C_1-C_6)$alkyl-S—, $(C_1-C_6)$alkyl-SO—, $(C_1-C_6)$alkyl-$SO_2$—; $(C_1-C_6)$alkyl-(C=O)—, $(C_6-C_{10})$aryl-(C=O)—, $(C_1-C_{10})$heteroaryl-(C=O)—, $(C_1-C_{10})$heterocyclyl-(C=O)—, $(C_1-C_6)$alkyl-NH—(C=O)—, $(C_6-C_{10})$aryl-NH—(C=O)—, or $[(C_1-C_6)$alkyl$]_2$-N—$SO_2$—;

Y is hydrogen, halogen, $-NO_2$, $(C_1-C_6)$alkyl, $-CF_3$, $(C_3-C_8)$cycloalkyl, $(C_1-C_6)$alkyl-O—, $(C_1-C_6)$alkyl-S—, $(C_1-C_6)$alkyl-SO—, $(C_1-C_6)$alkyl-$SO_2$—; $(C_1-C_6)$ alkyl-(C=O)—, $(C_6-C_{10})$aryl-(C=O)—, $(C_1-C_{10})$heteroaryl-(C=O)—, $(C_1-C_{10})$heterocyclyl-(C=O)—, $(C_1-C_6)$alkyl-NH—(C=O)—, $(C_6-C_{10})$aryl-NH—(C=O)—, or $[(C_1-C_6)$alkyl$]_2$-N—$SO_2$—;

n is 0, 1 or 2; preferably 0;

Q is a 6-membered heterocyclic divalent radical of pyran, piperidine, 1,4-dioxane, morpholine, dithiane, thiomorpholine, pyridazine, piperazine, pyridine, pyrimidine, pyrazine, 1,3,5-triazine, or 1,3,5-trithiane;

$R^1$ is hydrogen, halogen or $(C_1-C_6)$alkyl; and $R^2$ is $(C_1-C_6)$alkyl or $(C_3-C_8)$cycloalkyl.

The present invention also provides processes for the synthesis of compounds according to formula I.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine (meglumine), and the lower alkanolammonium and other base salts of pharmaceutically acceptable organic amines.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, para-toluenesulfonate and pamoate [i.e., 1,1'-methylene-bis-(2-hydroxy-3-naphthoate)]salts.

The compounds of this invention include all stereoisomers (e.g., cis and trans isomers) and all optical isomers of compounds of the formula I (e.g., R and S enantiomers), as well as racemic, diastereomeric and other mixtures of such isomers.

The compounds of the invention also exist in different tautomeric forms. This invention relates to all tautomers of formula I.

The compounds of this invention may contain olefin-like double bonds. When such bonds are present, the compounds of the invention exist as cis and trans configurations and as mixtures thereof.

Unless otherwise indicated, the term "$(C_1-C_6)$alkyl" as well as the $(C_1-C_6)$alkyl component of other terms referred to herein (e.g., the "$(C_1-C_6)$alkyl component of $(C_1-C_6)$alkyl-O—), may be linear or branched (such as methyl, ethyl, n-propyl, isopropyl, n-butyl, iso-butyl, secondary-butyl, tertiary-butyl), wherein each of said $(C_1-C_6)$alkyl component, wherever they occur, may optionally be substituted by one to three substituents per $(C_1-C_6)$alkyl component independently selected from the group consisting of fluoro, —OH, $(C_2-C_6)$alkenyl, $(C_2-C_6)$alkynyl, $(C_3-C_7)$cycloalkyl, $(C_1-C_6)$alkyl-O—, oxo, H—(C=O)—, $H_2$N—(C=O)—, $(C_1-C_6)$alkyl-(C=O)—, —CN, —$NO_2$, $(C_1-C_6)$alkyl-O—(C=O)—, $(C_1-C_6)$alkyl-NH—, $[(C_1-C_6)$alkyl$]_2$-N—, $(C_3-C_7)$cycloalkyl-NH—, $(C_6-C_{10})$aryl-NH—, $[(C_1-C_6)$alkyl]-$[((C_6-C_{10})$aryl)-N]—, $(C_1-C_9)$heteroaryl-NH—, $(C_1-C_{10})$heterocyclyl-NH—, $H_2$N—(C=O)—, $[(C_1-C_6)$alkyl]-NH—(C=O)—, $[(C_1-C_6)$alkyl$]_2$-N—(C=O)—, $[(C_6-C_{10})$aryl]-NH—(C=O)—, $[(C_1-C_6)$alkyl]-$[((C_6-C_{10})$aryl)-N]—(C=O)—, $(C_1-C_6)$alkyl-O—NH—(C=O)—, $(C_6-C_{10})$aryl, $(C_2-C_9)$heteroaryl, $(C_6-C_{10})$aryl-O—, $(C_1-C_9)$heteroaryl-O—, $(C_1-C_9)$heteroaryl-(C=O)—, $(C_1-C_6)$alkyl-S—, $(C_1-C_6)$alkyl-S(=O)—, $(C_1-C_6)$alkyl-$SO_2$—, $(C_1-C_6)$alkyl-(C=O)—NH—, $(C_1-C_6)$alkyl-(C=O)—NH—$(C_1-C_6)$alkyl-NH and $(C_1-C_6)$alkyl-(C=O)—O—.

Unless otherwise indicated, the term "halogen" means fluoro, chloro, bromo or iodo.

Unless otherwise indicated, the term "$(C_2-C_6)$alkenyl" means straight or branched hydrocarbon chain of 2 to 6 carbon atoms having at least one double bond including, but not limited to ethenyl, 1-propenyl, 2-propenyl(allyl), iso-propenyl, 2-methyl-1-propenyl, 1-butenyl, or 2-butenyl.

Unless otherwise indicated, the term "$(C_1-C_6)$alkylidene" has the formula =$CH_2$ or =$(CH_m)_n CH_3$ wherein m is 0 to 2 and n is 1 to 5, such as methylidine (=$CH_2$), ethylidine (=C—$CH_3$), propylidene (=CH—$CH_2CH_3$), or butylidene (=CH—$CH_2CH_2CH_3$). Said $(C_1-C_6)$alkylidene may be branched such as 1-methyl-ethylidine (=C($CH_3$)—$CH_3$).

Unless otherwise indicated, the term "$(C_2-C_6)$alkynyl" is used herein to mean straight or branched hydrocarbon chain of 2 to 6 carbon atoms having one triple bond including, but not limited to, ethynyl (—C≡C—H), propynyl (—$CH_2$—C≡C—H or —C≡C—$CH_3$), or butynyl (—$CH_2$—$CH_2$—C≡C—H, or —$CH_2$—C≡C—$CH_3$, or —C≡C—$CH_2CH_3$).

Unless otherwise indicated, the term "$(C_3-C_7)$cycloalkyl" refers to a mono or bicyclic carbocyclic ring including, but not limited to, cyclopropyl, cyclobutyl, cyclopentyl, cyclohexyl, cycloheptyl, and bicyclo[2.2.1]heptanyl; wherein said $(C_3-C_7)$cycloalkyl may optionally contain 1 or 2 double bonds including, but not limited to, cyclopentenyl, cyclohexenyl and cycloheptenyl.

Unless otherwise indicated, the term "$(C_6-C_{10})$aryl" means aromatic ring such as phenyl, naphthyl, tetrahydronaphthyl, or indanyl, wherein said $(C_6-C_{10})$aryl is optionally substituted on any ring carbon atom by one to two substituents per ring, wherein substituents are independently selected from the group consisting of halo, —OH, —CN, —SH, HO—(C=O)—, —$NO_2$, $(C_1-C_6)$alkyl, $(C_2-C_6)$alkenyl, $(C_2-C_6)$alkynyl, $(C_3-C_7)$cycloalkyl, $(C_6-C_{10})$aryl, $(C_1-C_9)$heteroaryl, $(C_1-C_9)$heterocyclyl, $(C_1-C_6)$alkyl-O—, —$OCF_3$, $(C_1-C_6)$alkyl-S—, $(C_1-C_6)$alkyl-NH—, $[(C_1-C_6)$alkyl$]_2$-N—, $(C_3-C_7)$cycloalkyl-NH—, $(C_6-C_{10})$aryl-NH—, $[(C_1-C_6)$alkyl]-$[((C_6-C_{10})$aryl)-N]—, $(C_1-C_9)$heteroaryl-NH—, $(C_1-C_{10})$heterocyclyl-NH—, $H_2$N—(C=O)—, $[(C_1-C_6)$alkyl]-NH—(C=O)—, $[(C_1-C_6)$alkyl$]_2$-N—(C=O)—, $[(C_6-C_{10})$aryl]-NH—(C=O)—, $[(C_1-C_6)$alkyl]-$[((C_6-C_{10})$aryl)-N]—(C=O)—, $(C_1-C_6)$alkyl-O—NH—(C=O)—, $(C_1-C_6)$alkyl-(C=O)—O—, $(C_1-C_6)$alkyl-(C=O)—NH—$(C_1-C_6)$alkyl-(C=O)—HN—$(C_1-C_6)$alkyl-NH, H—(C=O)—, $(C_1-C_6)$alkyl-(C=O)— and $(C_1-C_6)$alkyl-O—(C=O)—.

Unless otherwise indicated, the term "oxo" refers to =O.

Unless otherwise indicated, the term "$(C_1-C_9)$heteroaryl" refers to aromatic or multicyclic ring wherein at least one ring is aromatic, wherein said aromatic or multicyclic ring contains one or more heteroatoms selected from the group consisting of O, S and N. The $(C_1-C_9)$heteroaryl of this invention can also include ring systems substituted with one or more —(C=O)— substituents. Examples of heteroaryls include, but are not limited to, benzimidazolyl, benzofuranyl, benzofurazanyl, 2H-1-benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl, wherein said $(C_1-C_{10})$heteroaryl is optionally substituted on any atom(s) capable of forming an additional bond by one or two substituents independently selected from halo, —CN, —OH, $(C_1-C_6)$alkyl, perfluoro$(C_1-C_6)$alkyl, perfluoro$(C_1-C_6)$alkyl-O—, $(C_1-C_6)$alkyl-O— and $(C_3-C_8)$cycloalkyl-O—. Unless otherwise indicated, the foregoing $(C_1-C_9)$heteroaryls can be C-attached or N-attached where such is possible. For instance, pyrrolyl can be pyrrol-1-yl (N-attached) or pyrrol-3-yl (C-attached).

Unless otherwise indicated, the term "$(C_1-C_9)$heterocyclyl" refers to a cyclic ring containing 1 to 9 carbon atoms and 1 to 4 heteroatoms selected from the group consisting of N, O and S. The heterocyclyl ring can be optionally substituted where such is possible by substituents selected from the group consisting of oxo, —CN, —OH, $(C_1-C_6)$alkyl, perfluoro$(C_1-C_6)$alkyl, perfluoro$(C_1-C_6)$alkyl-O—, $(C_1-C_6)$alkyl-O— and $(C_3-C_8)$cycloalkyl-O—. Examples of the heterocyclyl rings include, but not limited to, 3-azabicyclo[3.1.0]hexanyl, 3-azabicyclo[4.1.0]-heptanyl, azetidinyl, dihydrofuranyl, dihydropyranyl, dihydrothienyl, dioxanyl, 1,3-dioxolanyl, 1,4-dithianyl, hexahydroazepinyl, hexahydropyrimidine, imidazolidinyl, imidazolinyl, isoxazolidinyl, morpholinyl, oxazolidinyl, piperazinyl, piperidinyl, 2H-pyranyl, 4H-pyranyl, pyrazolidinyl, pyrazolinyl, pyrrolidinyl, 2-pyrrolinyl, 3-pyrrolinyl, quinolizinyl, tetrahydrofuranyl, tetrahydropyranyl, 1,2,3,6-tetrahydropyridinyl, tetrahydrothienyl, tetrahydrothiopyranyl, thiomorpholinyl, thioxanyl or trithianyl. Unless otherwise indicated, the foregoing heterocyclyl functional group rings can be C-attached or N-attached where such is possible. For example, piperidinyl can be piperidin-1-yl (N-attached) or piperidin-4-yl (C-attached).

Preferably, Q is a 6-membered heterocyclic divalent radical of pyridine or pyrazine. More preferably, Q is 3-pyridinyl or 2-pyrazinyl and $R^2$ is $(C_1-C_6)$alkyl. Even more preferably, $R^1$ is hydrogen, halogen or $(C_1-C_6)$alkyl, and $R^2$ is $(C_1-C_6)$alkyl, and most preferably, $R^2$ is ethyl, propyl, or isopropyl.

Preferably, n is 0.

Preferably, X is hydrogen, fluoro or chloro.

Preferably, Y is hydrogen, fluoro or chloro.

More preferably, X is chloro, and Y is hydrogen.

Specific compounds of the present invention are the following:

5-Chloro-3-(5-methyl-pyrazine-2-carbonyl)-2-oxo-2,3-dihydro-indole-1-carboxylic acid ethylamide;
5-Chloro-2-oxo-3-(pyrazine-2-carbonyl)-2,3-dihydro-indole-1-carboxylic acid isopropylamide;
6-Chloro-3-(5-methyl-pyrazine-2-carbonyl)-2-oxo-2,3-dihydro-indole-1-carboxylic acid propylamide;
5-Chloro-3-(5-methyl-pyrazine-2-carbonyl)-2-oxo-2,3-dihydro-indole-1-carboxylic acid propylamide;
6-Chloro-5-fluoro-2-oxo-3-(pyrazine-2-carbonyl)-2,3-dihydro-indole-1-carboxylic acid propylamide;
3-(5-Methyl-pyrazine-2-carbonyl)-2-oxo-2,3-dihydro-indole-1-carboxylic acid butylamide;
5-Chloro-2-oxo-3-(pyrazine-2-carbonyl)-2,3-dihydro-indole-1-carboxylic acid propylamide;
6-Chloro-5-fluoro-2-oxo-3-(pyrazine-2-carbonyl)-2,3-dihydro-indole-1-carboxylic acid isopropylamide;
5-Chloro-2-oxo-3-(pyridine-3-carbonyl)-2,3-dihydro-indole-1-carboxylic acid isopropylamide;
3-(5-Methyl-pyrazine-2-carbonyl)-2-oxo-2,3-dihydro-indole-1-carboxylic acid propylamide;
5-Chloro-2-oxo-3-(pyrazine-2-carbonyl)-2,3-dihydro-indole-1-carboxylic acid tert-butylamide;
6-Chloro-5-fluoro-3-(5-methyl-pyrazine-2-carbonyl)-2-oxo-2,3-dihydro-indole-1-carboxylic acid isopropylamide;
5-Chloro-3-(5-methyl-pyrazine-2-carbonyl)-2-oxo-2,3-dihydro-indole-1-carboxylic acid butylamide;
5-Chloro-3-(5-methyl-pyrazine-2-carbonyl)-2-oxo-2,3-dihydro-indole-1-carboxylic acid tert-butylamide;
6-Chloro-2-oxo-3-(pyrazine-2-carbonyl)-2,3-dihydro-indole-1-carboxylic acid propylamide;
5-Chloro-2-oxo-3-(pyridine-3-carbonyl)-2,3-dihydro-indole-1-carboxylic acid tert-butylamide;
5-Chloro-3-(5-methyl-pyrazine-2-carbonyl)-2-oxo-2,3-dihydro-indole-1-carboxylic acid isopropylamide;
3-(5-Bromo-pyridine-3-carbonyl)-5-chloro-2-oxo-2,3-dihydro-indole-1-carboxylic acid isopropylamide;
3-(5-Bromo-pyridine-3-carbonyl)-2-oxo-2,3-dihydro-indole-1-carboxylic acid propylamide;
5-Chloro-2-oxo-3-(pyrazine-2-carbonyl)-2,3-dihydro-indole-1-carboxylic acid ethylamide;
3-(5-Bromo-pyridine-3-carbonyl)-2-oxo-2,3-dihydro-indole-1-carboxylic acid isopropylamide;
3-(5-Bromo-pyridine-3-carbonyl)-5-chloro-2-oxo-2,3-dihydro-indole-1-carboxylic acid propylamide;
5-Chloro-2-oxo-3-(pyrazine-2-carbonyl)-2,3-dihydro-indole-1-carboxylic acid cyclohexylamide;
5-Chloro-3-(5-methyl-pyrazine-2-carbonyl)-2-oxo-2,3-dihydro-indole-1-carboxylic acid cyclohexylamide; and
6-Chloro-3-(6-chloro-pyridine-3-carbonyl)-2-oxo-2,3-dihydro-indole-1-carboxylic acid ethylamide;
or the pharmaceutically-acceptable salts thereof.

Preferably, compounds of the present invention are:

5-Chloro-3-(5-methyl-pyrazine-2-carbonyl)-2-oxo-2,3-dihydro-indole-1-carboxylic acid ethylamide;
5-Chloro-2-oxo-3-(pyrazine-2-carbonyl)-2,3-dihydro-indole-1-carboxylic acid isopropylamide;
6-Chloro-3-(5-methyl-pyrazine-2-carbonyl)-2-oxo-2,3-dihydro-indole-1-carboxylic acid propylamide;
5-Chloro-3-(5-methyl-pyrazine-2-carbonyl)-2-oxo-2,3-dihydro-indole-1-carboxylic acid propylamide;
6-Chloro-5-fluoro-2-oxo-3-(pyrazine-2-carbonyl)-2,3-dihydro-indole-1-carboxylic acid propylamide;
3-(5-Methyl-pyrazine-2-carbonyl)-2-oxo-2,3-dihydro-indole-1-carboxylic acid butylamide;
5-Chloro-2-oxo-3-(pyrazine-2-carbonyl)-2,3-dihydro-indole-1-carboxylic acid propylamide;
6-Chloro-5-fluoro-2-oxo-3-(pyrazine-2-carbonyl)-2,3-dihydro-indole-1-carboxylic acid isopropylamide;
5-Chloro-2-oxo-3-(pyridine-3-carbonyl)-2,3-dihydro-indole-1-carboxylic acid isopropylamide;
3-(5-Methyl-pyrazine-2-carbonyl)-2-oxo-2,3-dihydro-indole-1-carboxylic acid propylamide; and
5-Chloro-2-oxo-3-(pyrazine-2-carbonyl)-2,3-dihydro-indole-1-carboxylic acid tert-butylamide;
or the pharmaceutically-acceptable salts thereof.

More preferably, compounds of the present invention are:

5-Chloro-3-(5-methyl-pyrazine-2-carbonyl)-2-oxo-2,3-dihydro-indole-1-carboxylic acid ethylamide;
6-Chloro-3-(5-methyl-pyrazine-2-carbonyl)-2-oxo-2,3-dihydro-indole-1-carboxylic acid propylamide;
6-Chloro-5-fluoro-2-oxo-3-(pyrazine-2-carbonyl)-2,3-dihydro-indole-1-carboxylic acid propylamide;
5-Chloro-2-oxo-3-(pyrazine-2-carbonyl)-2,3-dihydro-indole-1-carboxylic acid propylamide; and
3-(5-Methyl-pyrazine-2-carbonyl)-2-oxo-2,3-dihydro-indole-1-carboxylic acid propylamide;
or pharmaceutically-acceptable salts thereof.

Most preferably, the compound of the present invention is [-5-chloro-3-(5-methyl-pyrazine-2-carbonyl)-2-oxo-2,3-dihydro-indole-1-carboxylic acid ethylamide.

For the administration to canines, preferred compounds of the invention are

5-Chloro-3-(5-methyl-pyrazine-2-carbonyl)-2-oxo-2,3-dihydro-indole-1-carboxylic acid ethylamide;
5-Chloro-2-oxo-3-(pyrazine-2-carbonyl)-2,3-dihydro-indole-1-carboxylic acid isopropylamide;
6-Chloro-3-(5-methyl-pyrazine-2-carbonyl)-2-oxo-2,3-dihydro-indole-1-carboxylic acid propylamide;
5-Chloro-3-(5-methyl-pyrazine-2-carbonyl)-2-oxo-2,3-dihydro-indole-1-carboxylic acid propylamide;
6-Chloro-5-fluoro-2-oxo-3-(pyrazine-2-carbonyl)-2,3-dihydro-indole-1-carboxylic acid propylamide;
3-(5-Methyl-pyrazine-2-carbonyl)-2-oxo-2,3-dihydro-indole-1-carboxylic acid butylamide;
5-Chloro-2-oxo-3-(pyrazine-2-carbonyl)-2,3-dihydro-indole-1-carboxylic acid propylamide;
6-Chloro-5-fluoro-2-oxo-3-(pyrazine-2-carbonyl)-2,3-dihydro-indole-1-carboxylic acid isopropylamide;
5-Chloro-2-oxo-3-(pyridine-3-carbonyl)-2,3-dihydro-indole-1-carboxylic acid isopropylamide;
3-(5-Methyl-pyrazine-2-carbonyl)-2-oxo-2,3-dihydro-indole-1-carboxylic acid propylamide; and
5-Chloro-2-oxo-3-(pyrazine-2-carbonyl)-2,3-dihydro-indole-1-carboxylic acid tert-butylamide;
or the pharmaceutically-acceptable salts thereof.

For the administration to felines, preferred compounds of the present invention are:

5-Chloro-3-(5-methyl-pyrazine-2-carbonyl)-2-oxo-2,3-dihydro-indole-1-carboxylic acid ethylamide;
6-Chloro-3-(5-methyl-pyrazine-2-carbonyl)-2-oxo-2,3-dihydro-indole-1-carboxylic acid propylamide;

6-Chloro-5-fluoro-2-oxo-3-(pyrazine-2-carbonyl)-2,3-dihydro-indole-1-carboxylic acid propylamide;
3-(5-Methyl-pyrazine-2-carbonyl)-2-oxo-2,3-dihydro-indole-1-carboxylic acid butylamide;
5-Chloro-2-oxo-3-(pyrazine-2-carbonyl)-2,3-dihydro-indole-1-carboxylic acid propylamide;
6-Chloro-5-fluoro-2-oxo-3-(pyrazine-2-carbonyl)-2,3-dihydro-indole-1-carboxylic acid isopropylamide;
5-Chloro-2-oxo-3-(pyridine-3-carbonyl)-2,3-dihydro-indole-1-carboxylic acid isopropylamide; and
3-(5-Methyl-pyrazine-2-carbonyl)-2-oxo-2,3-dihydro-indole-1-carboxylic acid propylamide;
or the pharmaceutically-acceptable salts thereof.

In an embodiment of the present invention, the compound of formula I is administered in an amount of from about 0.5 mg/kg body weight/day to about 50 mg/kg body weight/day.

In another embodiment of the present invention, the compound of formula I is administered in an amount of from about 1 mg/kg body weight/day to about 10 mg/kg body weight/day.

The present invention also relates to an analgesic or anti-inflammatory pharmaceutical composition, containing a pharmaceutically-acceptable carrier and an effective analgesic or antiinflammatory amount of a compound of formula I, as defined above, or the pharmaceutically-acceptable salts thereof.

The present invention also relates to a pharmaceutical composition, useful as an analgesic and antiinflammatory agent in a mammalian subject, containing a pharmaceutically-acceptable carrier and an analgesic response eliciting or inflammatory disease treating amount of a compound of formula I, as defined above, or the pharmaceutically-acceptable salts thereof.

In a preferred embodiment of the aforesaid pharmaceutical composition, the weight ratio of the pharmaceutically-acceptable carrier to the effective analgesic amount of the compound or the effective antiinflammatory amount of the compound of the formula I is in the range from 1:4 to about 4:1.

The present invention also relates to a pharmaceutical composition, including one or more of the compounds of formula I and suitable carriers and/or additives. The compositions preferably contain an analgesic or antiinflammatory effective amount of a COX-2 selective inhibitor of formula I, or the pharmaceutically-acceptable salts thereof.

The present invention also provides a pharmaceutical composition containing at least one additional therapeutic agent for the treatment of osteoarthritis.

The present invention also provides a composition wherein the additional therapeutic agent for the treatment of osteoarthritis is selected from the group consisting of: piroxicam, diclofenac, propionic acids such as carprofen, naproxen, flurbiprofen, fenoprofen, ketoprofen, ibuprofen, mefenamic acid, indomethacin, sulindac, apazone, phenylbutazone, aspirin, celecoxib and rofecoxib, corticosteroids, hyalgan and synvisc.

The present invention also provides a pharmaceutical composition further containing at least one of the chondroprotective nutraceuticals for joint treatment selected from the group consisting of: polysulfated glycosaminoglycan (PSGAG), glucosamine, chondroitin sulfate (CS), hyaluronic acid (HA), and pentosan polysulfate (PPS).

The present invention also provides a method of treating an inflammatory disease or condition in a mammalian subject, by administering to said mammalian subject an inflammatory disease treating amount of a compound of formula I, as defined above, or the pharmaceutically-acceptable salts thereof.

The present invention also provides a method for treating or alleviating inflammation and inflammation related disorders, such as, for example, rheumatoid arthritis and osteoarthritis, and in the relief of pain, such as, for example, pain associated with surgery or trauma. The method includes administering to a subject in need of such treatment an effective amount of a compound of formula I or the pharmaceutically-acceptable salts thereof, or a composition containing a compound of formula I or the pharmaceutically-acceptable salts thereof.

The present invention also relates to a pharmaceutical composition for the treatment of a condition selected from the group consisting of arthritis (including osteoarthritis, degenerative joint disease, spondyloarthropathies, gouty arthritis, systemic lupus erythematosus, juvenile arthritis and rheumatoid arthritis), fever (including rheumatic fever and fever associated with influenza and other viral infections), common cold, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer; hematopoietic malignancies including leukemias and lymphomas; Hodgkin's disease; aplastic anemia, skin cancer and familiar adenomatous polyposis), tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), periarteritis nodosa, congestive heart failure, myocardial infarction, stroke, cerebral ischemia, head trauma, spinal cord injury, neuralgia, neuro-degenerative disorders (acute and chronic), autoimmune disorders, Huntington's disease, Parkinson's disease, migraine, depression, peripheral neuropathy, pain (including low back and neck pain, headache and toothache), gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders (such as psoriasis, eczema, scleroderma and dermatitis), myasthenia gravis, polymyositis, myositis, bursitis, burns, diabetes (including types I and II diabetes, diabetic retinopathy, neuropathy and nephropathy), tumor invasion, tumor growth, tumor metastasis, corneal scarring, scleritis, immunodeficiency diseases (such as AIDS in humans and FLV, FIV in felines), sepsis, premature labor, hypoprothrombinemia, hemophilia, thyroiditis, sarcoidosis, Behcet's syndrome, hypersensitivity, kidney disease, Rickettsial infections (such as Lyme disease, Erlichiosis), Protozoan diseases (such as malaria, giardia, coccidia), reproductive disorders (preferably in livestock) and septic shock (preferably arthritis, fever, common cold, pain and cancer) in a mammal, preferably a human, feline, livestock or a canine, comprising an amount of a compound of formula I or a pharmaceutically acceptable salt thereof effective in such treatment and a pharmaceutically acceptable carrier.

The present invention also relates to a pharmaceutical composition for the treatment of a condition that can be treated by selectively inhibiting COX-2 in a mammal, preferably a human, feline, livestock or canine, comprising a COX-2 selective inhibiting effective amount of a compound of formula I or a pharmaceutically acceptable salt thereof and a pharmaceutically acceptable carrier.

The present invention also relates to a pharmaceutical composition for the treatment of a condition selected from the group consisting of inflammatory diseases such as arthritis (including osteoarthritis, degenerative joint disease, spondyloarthropathies, gouty arthritis, systemic lupus erythematosus, juvenile arthritis and rheumatoid arthritis), or fever (including rheumatic fever and fever associated with influenza).

The present invention also relates to a method for treating a condition selected from the group consisting of arthritis (including osteoarthritis, degenerative joint disease, spondyloarthropathies, gouty arthritis, systemic lupus erythematosus, juvenile arthritis and rheumatoid arthritis), fever (including rheumatic fever and fever associated with influenza and other viral infections), common cold, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer; hematopoietic malignancies including leukemias and lymphomas; Hodgkin's disease; aplastic anemia, skin cancer and familiar adenomatous polyposis), tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), periarteritis nodosa, congestive heart failure, myocardial infarction, stroke, cerebral ischemia, head trauma, spinal cord injury, neuralgia, neuro-degenerative disorders (acute and chronic), autoimmune disorders, Huntington's disease, Parkinson's disease, migraine, depression, peripheral neuropathy, pain (including low back and neck pain, headache and toothache), gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders (such as psoriasis, eczema, scleroderma and dermatitis), myasthenia gravis, polymyositis, myositis, bursitis, burns, diabetes (including types I and II diabetes, diabetic retinopathy, neuropathy and nephropathy), tumor invasion, tumor growth, tumor metastasis, corneal scarring, scleritis, immunodeficiency diseases (such as AIDS in humans and FLV, FIV in felines), sepsis, premature labor, hypoprothrombinemia, hemophilia, thyroiditis, sarcoidosis, Behcet's syndrome, hypersensitivity, kidney disease, Rickettsial infections (such as Lyme disease, Erlichiosis), Protozoan diseases (such as malaria, giardia, coccidia), reproductive disorders (preferably in livestock) and septic shock (preferably arthritis, fever, common cold, pain, and cancer) in a mammal, preferably a human, feline, livestock or a canine, comprising administering to said mammal an amount of a compound of formula I or a pharmaceutically acceptable salt thereof effective in treating such a condition.

The present invention also relates to a method for treating a condition selected from the group consisting of inflammatory diseases such as arthritis (including osteoarthritis, degenerative joint disease, spondyloarthropathies, gouty arthritis, systemic lupus erythematosus, juvenile arthritis and rheumatoid arthritis), or fever (including rheumatic fever and fever associated with influenza).

The present invention also relates to a method for treating a disorder or condition that can be treated by selectively inhibiting COX-2 in a mammal, preferably a human, feline, livestock or a canine, comprising administering to a mammal requiring such treatment a COX-2 selective inhibiting effective amount of a compound of formula I or a pharmaceutically acceptable salt thereof.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "livestock animals" as used herein refers to domesticated quadripeds, which includes those being raised for meat and various byproducts, e.g., a bovine animal including cattle and other members of the genus *Bos*, a porcine animal including domestic swine and other members of the genus *Sus*, an ovine animal including sheep and other members of the genus *Ovis*, domestic goats and other members of the genus *Capra*; domesticated quadrupeds being raised for specialized tasks such as use as a beast of burden, e.g., an equine animal including domestic equines and other members of the family Equidae, genus *Equus*, or for searching and sentinel duty, e.g., a canine animal including domestic canines and other members of the genus *Canis*; and domesticated quadrupeds being raised primarily for recreational purposes, e.g., members of *Equus* and *Canis*, as well as a feline animal including domestic felines and other members of the family Felidae, genus *Felis*.

The term "Companion animals" as used herein refers to felines, canines and equines. As used herein, the term "canine(s)" denotes any member of the species *Canis familiaris*, of which there are a large number of different breeds. While laboratory determinations of biological activity may have been carried out using a particular breed, it is contemplated that the inhibitory compounds of the present invention will be found to be useful for treating pain and inflammation in any of these numerous breeds. Canines represent a particularly preferred class of patients in that they are well known as being very susceptible to chronic inflammatory processes such as osteoarthritis and degenerative joint disease, which in canines often results from a variety of developmental diseases, e.g., hip dysplasia and osteochondrosis, as well as from traumatic injuries to joints. Conventional NSAIDs, if used in canine therapy, have the potential for serious adverse gastrointestinal reactions and other adverse reactions including kidney and liver toxicity. Gastrointestinal effects such as single or multiple ulcerations, including perforation and hemorrhage of the esophagus, stomach, duodenum or small and large intestine, are usually debilitating, but can often be severe or even fatal.

The term "selective COX-2 inhibitor" as used herein, refers to COX-1/COX-2 $IC_{50}$ inhibition ratio of at least about 5 as determined for one of the in vitro, in vivo, or ex vivo assays described herein. The term denotes a compound able to inhibit COX-2 without significant inhibition of COX-1, e.g., the degree of inhibition of COX-2 compared to COX-1 inhibition that would be considered statistically significant by people of ordinary skill in this art. Preferably, it includes compounds which have a COX-2 $IC_{50}$ of less than about 25 $\mu M$, and also have a selectivity ratio of COX-1 inhibition over COX-2 inhibition of at least about 5, and more preferably of at least about 25. Preferably, the compounds have a COX-1 $IC_{50}$ of greater than about 10 $\mu$M, and more preferably of greater than about 100 $\mu$M.

The term "treating reproductive disorders (preferably in livestock)" as used herein refers to the use of the COX-2 inhibitors of the invention in mammals, preferably livestock animals (cattle, pigs, sheep, goats or equines), during the estrus cycle to control the time of onset of estrus by blocking the uterine signal for lysis of the corpus luteum, i.e. F-series prostaglandins, then removing the inhibition when the onset of estrus is desired. There are settings where it is useful to control or synchronize the time of estrus, especially when artificial insemination or embryo transfer are to be performed. Such use also includes enhancing the rate of embryo survival in pregnant livestock animals. Blocking F-series prostaglandin release can have several beneficial actions including reducing uterine contractions, enhancing uteroplacental bloodflow, supporting recognition of pregnancy and postponing lysis of the corpus luteum at the time when estrus would have occurred had the animal not become pregnant (around day 21 of pregnancy). Such treatment also abrogates the effects of stress on reproduction. For example reductions in fertility caused by excessive heat, negative energy balance and other stresses which have a COX-2 mediated component, as does abortion induced by stress such as heat, transportation, co-mingling, palpation, infection, etc. Such treatment is also useful to control the time of parturition, which is accompanied by release of F-series prostaglandins that lead to lysis of the corpus luteum. Inhibition of COX-2 would block the onset of premature labor in livestock animals, allowing the offspring time to mature before birth. Also there are settings where controlling the time of parturition is a useful tool for management of pregnant animals.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present invention, prodrugs thereof and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$ and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing prodrugs of compounds of the formula I.

This invention also encompasses methods of treating disorders that can be treated by the selective inhibition of COX-2 comprising administering prodrugs of compounds of the formula I. Compounds of formula I having free amino, amido, hydroxy, carboxylic acid ester, sulfonamide or carboxylic groups (especially alkyl-S— and alkyl-(S=O)—) can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters are covalently bonded to the above substituents of formula I through the carbonyl carbon prodrug sidechain. Prodrugs also include metabolically labile groups such as ethers, acetates, mercaptans and sulfoxides.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies and TNF receptor immunoglobulin molecules (such as Enbrel®), low dose methotrexate, lefunimide, hydroxychloroquine, d-penicilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as carprofen, naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib and rofecoxib, analgesics and intraarticular therapies such as corticosteroids and hyaluronic acids such as hyalgan and synvisc. In addition compounds of the invention may be combined with one or more members selected from the group of chondroprotective nutraceuticals consisting essentially of polysulfated glycosaminoglycan (PSGAG), glucosamine, chondroitin sulfate (CS), hyaluronic acid (HA), and pentosan polysulfate (PPS).

This invention also relates to a method of or a pharmaceutical composition for treating inflammatory processes and diseases comprising administering a compound of formula I of this invention or its salt to a mammal including a human, feline, livestock or canine, wherein said inflammatory processes and diseases are defined as above and said inhibitory compound is used in combination with one or more other therapeutically active agents under the following conditions:

A.) where a joint has become seriously inflamed as well as infected at the same time by bacteria, fungi, protozoa and/or virus, said inhibitory compound is administered in combination with one or more antibiotic, antifungal, antiprotozoal and/or antiviral therapeutic agents;

B.) where a multi-fold treatment of pain and inflammation is desired, said inhibitory compound is administered in combination with inhibitors of other mediators of inflammation, comprising one or more members independently selected from the group consisting essentially of:

(1) NSAIDs;
(2) $H_1$-receptor antagonists;
(3) kinin-$B_1$- and $B_2$-receptor antagonists;
(4) prostaglandin inhibitors selected from the group consisting of PGD-, PGF- $PGI_2$- and PGE-receptor antagonists;
(5) thromboxane $A_2$ ($TXA_2$-) inhibitors;
(6) 5-, 12- and 15-lipoxygenase inhibitors;
(7) leukotriene $LTC_4$-, $LTD_4/LTE_4$- and $LTB_4$-inhibitors;
(8) PAF-receptor antagonists;
(9) gold in the form of an aurothio group together with one or more hydrophilic groups;
(10) immunosuppressive agents selected from the group consisting of cyclosporine, azathioprine and methotrexate;
(11) anti-inflammatory glucocorticoids;
(12) penicillamine;
(13) hydroxychloroquine;
(14) anti-gout agents including colchicine; xanthine oxidase inhibitors including allopurinol; and uricosuric agents selected from probenecid, sulfinpyrazone and benzbromarone;

C.) where older mammals are being treated for disease conditions, syndromes and symptoms found in geriatric mammals, said inhibitory compound is administered in combination with one or more members independently selected from the group consisting essentially of:

(1) cognitive therapeutics to counteract memory loss and impairment;
(2) anti-hypertensives and other cardiovascular drugs intended to offset the consequences of atherosclerosis, hypertension, myocardial ischemia, angina, congestive heart failure and myocardial infarction, selected from the group consisting of:
 a. diuretics;
 b. vasodilators;
 c. β-adrenergic receptor antagonists;
 d. angiotensin-II converting enzyme inhibitors (ACE-inhibitors), alone or optionally together with neutral endopeptidase inhibitors;
 e. angiotensin II receptor antagonists;
 f. renin inhibitors;
 g. calcium channel blockers;
 h. sympatholytic agents;
 i. $α_2$-adrenergic agonists;
 j. α-adrenergic receptor antagonists; and
 k. HMG-CoA-reductase inhibitors (anti-hypercholesterolemics);
(3) antineoplastic agents selected from:
 a. antimitotic drugs selected from:
 i. vinca alkaloids selected from:
 [1] vinblastine and
 [2] vincristine;

(4) growth hormone secretagogues;
(5) strong analgesics;
(6) local and systemic anesthetics; and
(7) $H_2$-receptor antagonists, proton pump inhibitors and other gastroprotective agents.

The active ingredient of the present invention may be administered in combination with inhibitors of other mediators of inflammation, comprising one or more members selected from the group consisting essentially of the classes of such inhibitors and examples thereof which include, matrix metalloproteinase inhibitors, aggrecanase inhibitors, TACE inhibitors, leukotriene receptor antagonists, IL-1 processing and release inhibitors, ILra, $H_1$-receptor antagonists; kinin-$B_1$- and $B_2$-receptor antagonists; prostaglandin inhibitors such as PGD-, PGF- $PGI_2$- and PGE-receptor antagonists; thromboxane $A_2$ (TXA2-) inhibitors; 5- and 12-lipoxygenase inhibitors; leukotriene $LTC_4$-, $LTD_4/LTE_4$- and $LTB_4$-inhibitors; PAF-receptor antagonists; gold in the form of an aurothio group together with various hydrophilic groups; immunosuppressive agents, e.g., cyclosporine, azathioprine and methotrexate; anti-inflammatory glucocorticoids; penicillamine; hydroxychloroquine; anti-gout agents, e.g., colchicine, xanthine oxidase inhibitors, e.g., allopurinol and uricosuric agents, e.g., probenecid, sulfinpyrazone and benzbromarone.

The compounds of the present invention may also be used in combination with chondroprotective nutraceuticals for joint treatment such as polysulfated glycosaminoglycan (PSGAG), glucosamine, chondroitin sulfate (CS), hyaluronic acid (HA), and pentosan polysulfate (PPS).

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine and antimetabolites such as methotrexate.

The compounds of the present invention may also be used in combination with anti-hypertensives and other cardiovascular drugs intended to offset the consequences of atherosclerosis, including hypertension, myocardial ischemia including angina, congestive heart failure and myocardial infarction, selected from vasodilators such as hydralazine, β-adrenergic receptor antagonists such as propranolol, calcium channel blockers such as nifedipine, $α_2$-adrenergic agonists such as clonidine, α-adrenergic receptor antagonists such as prazosin and HMG-CoA-reductase inhibitors (anti-hypercholesterolemics) such as lovastatin or atorvastatin.

The active ingredient of the present invention may also be administered in combination with one or more antibiotic, antifungal, antiprotozoal, antiviral or similar therapeutic agents.

The compounds of the present invention may also be used in combination with CNS agents such as antidepressants (such as sertraline), anti-Parkinsonian drugs (such as L-dopa, requip, mirapex, MAOB inhibitors such as selegine and rasagiline, comP inhibitors such as Tasmar, A-2 inhibitors, dopamine reuptake inhibitors, NMDA antagonists, nicotine agonists, dopamine agonists and inhibitors of neuronal nitric oxide synthase) and anti-Alzheimer's drugs such as donepezil, tacrine, COX-2 inhibitors, propentofylline or metryfonate.

The compounds of the present invention may also be used in combination with osteoporosis agents such as roloxifene, lasofoxifene, droloxifene or fosomax and immunosuppressant agents such as FK-506 and rapamycin.

The present invention also relates to the formulation of the active agents of the present invention alone or with one or more other therapeutic agents which are to form the intended combination, including wherein said different drugs have varying half-lives, by creating controlled-release forms of said drugs with different release times which achieves relatively uniform dosing; or, in the case of non-human patients, a medicated feed dosage form in which said drugs used in the combination are present together in admixture in said feed composition. There is further provided in accordance with the present invention co-administration in which the combination of drugs is achieved by the simultaneous administration of said drugs to be given in combination; including co-administration by means of different dosage forms and routes of administration; the use of combinations in accordance with different but regular and continuous dosing schedules whereby desired plasma levels of said drugs involved are maintained in the patient being treated, even though the individual drugs making up said combination are not being administered to said patient simultaneously.

DETAILED DESCRIPTION OF THE INVENTION

As discussed above, this invention relates to the compounds of formula I, and these compounds are named as derivatives of 2-oxindole, the compound of formula II having the ring numbering designations set forth below:

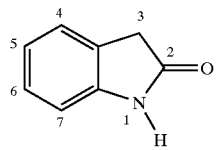

(II)

More particularly, the analgesic and anti-inflammatory agents of formula I have a carboxamide substituent, —C(=O)—NH—$R^2$, at the 1-position and an acyl substituent, —C(=O)—$(CH_2)_n$—Q—$R^1$, at the 3-position of 2-oxindole, and the benzo ring can be further substituted by X and Y groups at positions 5 and 6, respectively. X and Y can be certain monovalent substituents as defined previously. Q can be certain 6 membered heterocyclic divalent radicals as defined previously.

Additionally, as will be appreciated by one skilled in the art, the analgesic and anti-inflammatory compounds of formula I, wherein X, Y, $R^1$, $R^2$ and Q, are defined previously, are capable of enolization, and therefore they can exist in one or more tautomeric (enolic) forms. All such tautomeric (enolic) forms of the compounds of formula I are considered to be within the scope of this invention.

The compounds of the formula I are prepared from the appropriate 2-oxindole compound of the formula III:

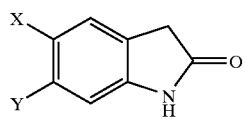

(III)

wherein X and Y are as defined previously. This is accomplished by attaching the substituent —C(=O)—NH—$R^2$ to the nitrogen (1-position) and the —C(=O)—$(CH_2)_n$—Q—$R^1$ substituent to the 3-position. These substituents can be attached in either order, and this leads to two variations in the method for making the compounds of formula I, as shown in the Scheme I set forth below:

SCHEME I

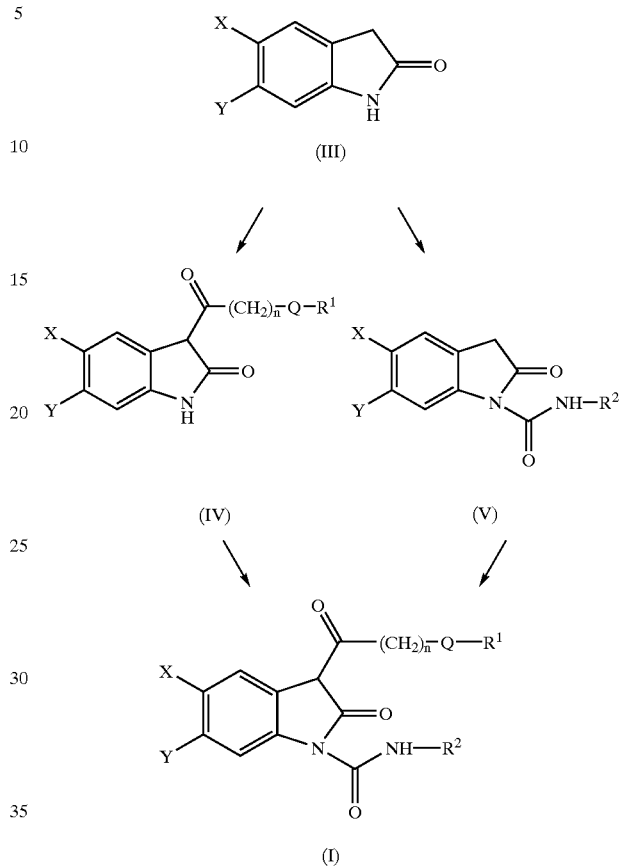

Those skilled in the art will appreciate that the above scheme I describes general methods for preparing the compounds of the invention. Specific compounds of formula I may possess sensitive functional groups that require protecting groups when prepared with the intermediates described. Examples of suitable protecting groups may be found in T. W. Greene and P. Wuts, Protecting Groups in Organic Synthesis, John Wiley & Sons, 2nd Edition, New York, 1991.

Referring to Scheme I, the first variation of the preparation of the compounds of formula I involves converting compounds of formula III to compounds of formula IV, and then converting compounds of formula IV to compounds of formula I. The second variation involves converting compounds of formula III to compounds of formula V, and then converting compounds of formula V to compounds of formula I. Preferably, the second variation is used to make the compounds of the present invention.

Referring to the second variation, compounds of formula I can be prepared by reacting a compound of formula V with one molar equivalent or a slight excess of an activated acid in the presence of from one to four equivalents of a basic agent in an inert solvent or a polar aprotic solvent. Suitable activated acids include acid halides of formula $R^1$—Q—$(CH_2)_n$—C(=O)—X, wherein X is halo, such as chloro; symmetrical acid anhydrides of formula $R^1$—Q—$(CH_2)_n$—C(=O)—O—C(=O)—$(CH_2)_n$—Q—$R^1$; mixed acid anhydrides of formula $R^1$—Q—$(CH_2)_n$—C(=O)—O—C(=O)—$(CH_2)_n$—Q—$R^3$, wherein $R^3$ is a bulky lower-alkyl group such as t-butyl; and mixed carboxylic-carbonic anhydrides of formula $R^1$—Q—$(CH_2)_n$—C(=O)—O—C(=O)—$(CH_2)_n$—Q—$OR^4$, wherein $R^4$ is a lower alkyl group. Other suitable activated acids include N-hydroxyimide esters (such as N-hydroxysuccinimide or N-hydroxyphthalimide esters); 4-nitrophenyl esters; thiol esters (such as thiol phenyl esters); 2,4,5-trichlorophenyl esters, and the like. Suitable inert solvent is one which will dissolve at least one of the reactants, and will not adversely interact with either of the reactants or the product. Example of inert solvents which can be used include aliphatic hydrocarbons, such as octane, nonane, decane and decalin; aromatic hydrocarbons, such as benzene, chlorobenzene, toluene, xylenes and tetralin; chlorinated hydrocarbons, such as 1,2-dichloroethane; ethers, such as tetrahydrofuran, dioxane, 1,2-dimethoxyethane and di(2-methoxyethyl)ether; and polar aprotic solvents such as N,N-dimethylformamide, N,N-dimethylacetamide, N-methylpyrrolidone and dimethyl sulfoxide. Suitable polar aprotic solvent includes N,N-dimethylformamide, N,N-dimethylacetamide, N-methylpyrrolidone or dimethyl sulfoxide. Suitable basic agents include amines, preferably tertiary amines, such as trimethylamine, triethylamine, tributylamine, N-methylmorpholine, N-methylpiperidine and 4-(N,N-dimethylamino)pyridine. The aforesaid reaction can be conducted from about −10° C. to about 25° C. The aforesaid reaction can be conducted from 30 minutes to a few hours. At the end of the aforesaid reaction, the reaction medium is usually diluted with water and acidified, and then the product can be recovered by filtration. The product can be purified by standard methods, such as recrystallization.

The above activated acids can be prepared by conventional methods from an acid of formula $R^1$—Q—$(CH_2)_n$—C(=O)OH.

A compound of the formula V can be prepared by reacting a compound of formula III with an isocyanate of the formula $R^2$—N=C=O, in the presence of an inert solvent. Suitable inert solvent include a solvent that will dissolve at least one of the reactants, and which does not adversely interact with either of the reactants or the product. Example of inert solvents which can be used include aliphatic hydrocarbons, such as octane, nonane, decane and decalin; aromatic hydrocarbons, such as benzene, chlorobenzene, toluene, xylenes and tetralin; chlorinated hydrocarbons, such as 1,2-dichloroethane; ethers, such as tetrahydrofuran, dioxane, 1,2-dimethoxyethane and di(2-methoxyethyl)ether; and polar aprotic solvents such as N,N-dimethylformamide, N,N-dimethylacetamide, N-methylpyrrolidone and dimethyl sulfoxide. The aforesaid reaction can be conducted at a temperature in the range of from about 50° C. to about 150° C., preferably from about 100° C. to about 130° C. The reaction time varies according to the reaction temperature. At a temperature of from about 100° C. to about 130° C., reaction times of a few hours, such as, for example, 5 hours to 10 hours, are commonly used.

In the aforesaid preparation of the compound of formula V, when a relatively non-polar reaction solvent is used, the product compound of the formula V is usually out of solution at the end of the reaction upon cooling to room temperature. Under these circumstances the product is usually recovered by filtration. Alternatively, when a relatively polar solvent is used and the product is not out of solution at the end of the reaction, the product compound of the formula V can be recovered by solvent evaporation. Yet alternatively, when a water-miscible solvent is used and the product is not out of solution at the end of the reaction, the product compound of the formula V can be precipitated by diluting the reaction medium with water, and again the product can be recovered by filtration. The reaction product of formula V can be purified by standard methods, e.g., recrystallization.

Referring to the first variation, a compound of the formula I can prepared by reacting a compound of the formula IV with an isocyanate of the formula $R^2$—N=C=O, in the presence of an inert solvent. The procedure for this preparation is analogous to the above description of the preparation of the compound of formula V from the compound of formula III.

A compound of the formula IV can be prepared by reacting a compound of the formula III with an activated acid in a lower-alkanol solvent (e.g., ethanol) and in the presence of an alkali metal salt of the lower-alkanol solvent (e.g., sodium ethoxide), according to standard procedures. Suitable activated acids include acid chlorides of the formula $R^1$—Q—$(CH_2)_n$—C(=O)—X, wherein X is halo, such as chloro; symmetrical acid anhydrides of the formula $R^1$—Q—$(CH_2)_n$—C(=O)—O—C(=O)—$(CH_2)_n$—Q—$R^1$; mixed acid anhydrides of the formula $R^1$—Q—$(CH_2)_n$—C(=O)—O—C(=O)—$(CH_2)_n$—Q—$R^3$, wherein $R^3$ is a bulky lower-alkyl group such as t-butyl; mixed carboxylic-carbonic anhydrides of the formula $R^1$—Q—$(CH_2)_n$—C(=O)—O—C(=O)—$(CH_2)_n$—Q—$OR^4$, wherein $R^4$ is a lower alkyl group; and alkyl esters of the formula $R^1$—Q—$(CH_2)_n$—C(=O)—$OR^5$, wherein $R^5$ is a lower alkyl group. Preferably, a small excess of the activated acid is used. Preferably, the alkali metal salt of the lower-alkanol solvent is present in an amount from one to two molar equivalents, based on the amount of the activated acid. The aforesaid reaction can be conducted at a starting temperature of about 0° C. to about 25° C., which is then usually increased to a range of from about 50° C. to about 130° C., and preferably at about 80° C., to complete the reaction. The aforesaid reaction can be conducted for a period of a few hours, e.g., two hours, up to a few days, e.g., two days. The reaction mixture is then cooled, diluted with an excess of water, and acidified. The product of formula IV can then be recovered by filtration or by the standard procedure of solvent extraction.

The aforesaid reaction between a compound of formula IV and an isocyanate of formula $R^2$—N=C=O can be accelerated by the addition of a basic agent. Suitable basic agent includes a tertiary amine, such as trimethylamine, triethylamine, tributylamine, N-methylpiperidine, N-methylmorpholine or N,N-dimethylaniline. From about one to about four equivalents of the basic agent are usually added, and this permits the use of reaction temperature of from about 20° C. to about 50° C. At the end of the reaction, the reaction medium must be neutralized (or made acidic) and then the product is isolated as described earlier.

The isocyanates of the formula $R^2$—N=C=O can be prepared by standard procedures. See further: "Organic Functional Group Preparations" by Sandler and Karo, Part I, Second Edition, Academic Press, Inc., New York, N.Y., 1983, Chapter 12, pp. 364–369. A particularly useful method involves reaction of the appropriate amine of formula $R^2$—$NH_2$ with phosgene:

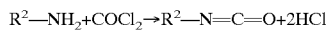

$R^2$—$NH_2$+$COCl_2$→$R^2$—N=C=O+2HCl

Many of the isocyanates of formula $R^2$—N=C=O are known in the prior art.

The compounds of formula III are prepared by known methods, or methods analogous to known methods. Consult: "Rodd's Chemistry of Carbon Compounds," Second Edition, S. Coffey editor, Volume IV Part A, Elsevier Scientific Publishing Company, 1973, pp. 448–450; Gassman et al., Journal of Organic Chemistry, 42, 1340 (1977); Wright et al., Journal of the American Chemical Society, 78, 221 (1956); Beckett et al., Tetrahedron, 24, 6093 (1968); U.S. Pat. Nos. 3,882,236, 4,006,161 and 4,160,032; Walker, Journal of the American Chemical Society, 77, 3844 (1955); Protiva et al., Collection of Czechoslovakian Chemical Communications, 44, 2108 (1979); McEvoy et al., Journal of Organic Chemistry, 38, 3350 (1973); Simet, Journal of Organic Chemistry, 28, 3580 (1963); Wieland et al., Chemische Berichte, 96, 253 (1963); and references cited therein. All the above references are incorporated herein by reference.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations and then evaporating the resulting solution to dryness, preferably under reduced pressure. Alternatively, they may also be prepared by mixing lower alkanolic solutions of the acidic compounds and the desired alkali metal alkoxide together and then evaporating the resulting solution to dryness in the same manner as before. In either case, stoichiometric quantities of reagents are preferably employed in order to ensure completeness of reaction and maximum product yields.

The compounds of formula I of the invention can be used in a pharmaceutical composition for the treatment of a condition selected from the group consisting of arthritis (including osteoarthritis, degenerative joint disease, spondyloarthropathies, gouty arthritis, systemic lupus erythematosus, juvenile arthritis and rheumatoid arthritis), fever (including rheumatic fever and fever associated with influenza and other viral infections), common cold, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer; hematopoietic malignancies including leukemias and lymphomas; Hodgkin's disease; aplastic anemia, skin cancer and familiar adenomatous polyposis), tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), periarteritis nodosa, congestive heart failure, myocardial infarction, stroke, cerebral ischemia, head trauma, spinal cord injury, neuralgia, neuro-degenerative disorders (acute and chronic), autoimmune disorders, Huntington's disease, Parkinson's disease, migraine, depression, peripheral neuropathy, pain (including low back and neck pain, headache and toothache), gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders (such as psoriasis, eczema, scleroderma and dermatitis), myasthenia gravis, polymyositis, myositis, bursitis, burns, diabetes (including types I and II diabetes, diabetic retinopathy, neuropathy and nephropathy), tumor invasion, tumor growth, tumor metastasis, corneal scarring, scleritis, immunodeficiency diseases (such as AIDS in humans and FLV, FIV in felines), sepsis, premature labor, hypoprothrombinemia, hemophilia, thyroiditis, sarcoidosis, Behcet's syndrome, hypersensitivity, kidney disease, Rickettsial infections (such as Lyme disease, Erlichiosis), Protozoan diseases (such as malaria, giardia, coccidia), reproductive disorders (preferably in livestock) and septic shock (preferably arthritis, fever, common cold, pain and cancer) in a mammal, preferably a human, feline, livestock or a canine, comprising an amount of a compound of formula I or a pharmaceutically acceptable salt thereof effective in such treatment and a pharmaceutically acceptable carrier.

The compounds of formula I of the invention can also be used in a pharmaceutical composition for the treatment of a disorder or condition that can be treated by selectively inhibiting COX-2 in a mammal, preferably a human, feline, livestock or canine, comprising an effective amount of a compound of formula I or a pharmaceutically acceptable salt thereof and a pharmaceutically acceptable carrier.

The compounds of formula I of the invention can also be used in a pharmaceutical composition for the treatment of a condition selected from the group consisting of inflammatory diseases such as arthritis (including osteoarthritis, degenerative joint disease, spondyloarthropathies, gouty arthritis, systemic lupus erythematosus, juvenile arthritis and rheumatoid arthritis), or fever (including rheumatic fever and fever associated with influenza).

The compound of the present invention, alone or in a pharmaceutical composition, may be administered in single or divided doses.

The pharmaceutical composition of the present invention may preferably contain active ingredient in an amount ranging from about 0.1 mg to about 2000 mg, more preferably from about 0.5 mg to about 500 mg, and most preferably from about 1 mg to about 100 mg.

The compounds of the present invention, alone or in a pharmaceutical composition, may be administered to a subject that is preferably a mammal, more preferably a human, canine, feline, equine, or bovine, most preferably a canine or feline.

The compounds of the present invention may be administered to a human to treat osteoarthritis at 200 mg/day in single or multiple doses.

The compounds of formula I of the invention can also be used in a method for treating a condition selected from the group consisting of arthritis (including osteoarthritis, degenerative joint disease, spondyloarthropathies, gouty arthritis, systemic lupus erythematosus, juvenile arthritis and rheumatoid arthritis), fever (including rheumatic fever and fever associated with influenza and other viral infections), common cold, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer; hematopoietic malignancies including leukemias and lymphomas; Hodgkin's disease; aplastic anemia, skin cancer and familiar adenomatous polyposis), tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), periarteritis nodosa, congestive heart failure, myocardial infarction, stroke, cerebral ischemia, head trauma, spinal cord injury, neuralgia, neuro-degenerative disorders (acute and chronic), autoimmune disorders, Huntington's disease, Parkinson's disease, migraine, depression, peripheral neuropathy, pain (including low back and neck pain, headache and toothache), gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders (such as psoriasis, eczema, scleroderma and dermatitis), myasthenia gravis, polymyositis, myositis, bursitis, burns, diabetes (including types I and II diabetes, diabetic retinopathy, neuropathy and nephropathy), tumor invasion, tumor growth, tumor metastasis, corneal scarring, scleritis, immunodeficiency diseases (such as AIDS in humans and FLV, FIV in felines), sepsis, premature labor, hypoprothrombinemia, hemophilia, thyroiditis, sarcoidosis, Behcet's syndrome, hypersensitivity, kidney disease, Rickettsial infections (such as Lyme disease, Erlichiosis), Protozoan diseases (such as malaria, giardia, coccidia), reproductive disorders (preferably in livestock) and septic shock (preferably arthritis, fever, common cold, pain and cancer) in a mammal, preferably a human, feline, livestock or a canine, comprising administering to said mammal an amount of a compound of formula I or a pharmaceutically acceptable salt thereof effective in treating such a condition.

The compounds of formula I of the invention can also be used in a method for treating a disorder or condition that can be treated by selectively inhibiting COX-2 in a mammal, preferably a human, feline, livestock or a canine, comprising administering to a mammal requiring such treatment a COX-2 selective inhibiting effective amount of a compound of formula I or a pharmaceutically acceptable salt thereof.

The compounds of the present invention can also be used for ameliorating or eliminating pain, such as the pain experienced by subjects as a result of surgery or trauma.

In addition, the compounds of the present invention can also be used for alleviating the symptoms of chronic diseases, such as the inflammation and pain associated with chronic diseases, such as, for example, rheumatoid arthritis, osteoarthritis and other musculoskeletal disorders.

Method for Assessing Biological Activities

The activity of the compounds of the formula I of the present invention may be demonstrated by the following assays.

Human In Vitro Assays

Human Cell-based COX-1 Assay

Human peripheral blood obtained from healthy volunteers can be diluted to $\frac{1}{10}$ volume with 3.8% sodium citrate solution. The platelet-rich plasma immediately obtained can be washed with 0.14 M sodium chloride containing 12 mM Tris-HCl (pH 7.4) and 1.2 mM EDTA. Platelets can then be washed with platelet buffer (Hanks buffer (Ca free) containing 0.2% BSA and 20 mM Hepes). Finally, the human washed platelets (HWP) can be suspended in platelet buffer at the concentration of $2.85 \times 10^8$ cells/ml and stored at room temperature until use. The HWP suspension (70 $\mu$l aliquots, final $2.0 \times 10^7$ cells/ml) can be placed in a 96-well U bottom plate and 10 $\mu$l aliquots of 12.6 mM calcium chloride added. Platelets can be incubated with A23187 (final 10 $\mu$M, Sigma) with test compound (0.1–100 $\mu$M) dissolved in DMSO (final concentration; less than 0.01%) at 37° C. for 15 minutes. The reaction can be stopped by addition of EDTA (final 7.7 mM) and TxB2 in the supernatant quantitated by using a radioimmunoassay kit (Amersham) according to the manufacturer's procedure.

Human Cell-based COX-2 Assay

The human cell based COX-2 assay can be carried out as previously described (Moore et al., Inflam. Res., 45, 54, 1996). Confluent human umbilical vein endothelial cells (HUVECs, Morinaga) in a 96-well flat bottom plate can be washed with 80 ml of RPMI1640 containing 2% FBS and incubated with hIL-1β (final concentration 300 U/ml, R & D Systems) at 37° C. for 24 hours. After washing, the activated HUVECs can be incubateed with test compound (final concentration; 0.1 nM-1 $\mu$M) dissolved in DMSO (final concentration; less than 0.01%) at 37° C. for 20 minutes and stimulated with A23187 (final concentration 30 mM) in Hanks buffer containing 0.2% BSA, 20 mM Hepes at 37° C. for 15 minutes. 6-Keto-PGF$_{1\alpha}$, stable metabolite of PGI2, in the supernatant can be quantitated by using a radioimmunoassay method (antibody; Preseptive Diagnostics, SPA; Amersham).

Canine In Vitro Assays

The following canine cell based COX 1 and COX-2 assays have been reported in Ricketts et al., *Evaluation of Selective Inhibition of Canine Cyclooxygenase 1 and 2 by Carprofen and Other Nonsteroidal Anti-inflammatory Drugs*, American Journal of Veterinary Research, 59 (11), 1441–1446.

Protocol for Evaluation of Canine COX-1 Activity

Test drug compounds can be solubilized and diluted the day before the assay can be to be conducted with 0.1 mL of DMSO/9.9 mL of Hank's balanced salts solution (HBSS) and stored overnight at 4° C. On the day that the assay can be carried out, citrated blood can be drawn from a donor canine, centrifuged at 190×g for 25 minutes at room temperature and the resulting platelet-rich plasma can then be transferred to a new tube for further procedures. The platelets can be washed by centrifuging at 1500×g for 10 minutes at room temperature. The platelets can be washed with platelet buffer comprising Hank's buffer (Ca free) with 0.2% bovine serum albumin (BSA) and 20 mM HEPES. The platelet samples can then be adjusted to $1.5 \times 10^7$/mL, after which 50 µl of calcium ionophore (A23187) together with a calcium chloride solution can be added to 50 µl of test drug compound dilution in plates to produce final concentrations of 1.7 µM A23187 and 1.26 mM Ca. Then, 100 µl of canine washed platelets can be added and the samples can be incubated at 37° C. for 15 minutes, after which the reaction can be stopped by adding 20 µl of 77 mM EDTA. The plates can then be centrifuged at 2000×g for 10 minutes at 4° C., after which 50 µl of supernatant can be assayed for thromboxane $B_2$ ($TXB_2$) by enzyme-immunoassay (EIA). The pg/mL of $TXB_2$ can be calculated from the standard line included on each plate, from which it can be possible to calculate the percent inhibition of COX-1 and the $IC_{50}$ values for the test drug compounds.

Protocol for Evaluation of Canine COX-2 Activity

A canine histocytoma (macrophage-like) cell line from the American Type Culture Collection designated as DH82, can be used in setting up the protocol for evaluating the COX-2 inhibition activity of various test drug compounds. There can be added to flasks of these cells 10 µg/mL of LPS, after which the flask cultures can be incubated overnight. The same test drug compound dilutions as described above for the COX-1 protocol can be used for the COX-2 assay and can be prepared the day before the assay can be carried out. The cells can be harvested from the culture flasks by scraping and can then be washed with minimal Eagle's media (MEM) combined with 1% fetal bovine serum, centrifuged at 1500 rpm for 2 minutes and adjusted to a concentration of $3.2 \times 10^5$ cells/mL. To 50 µl of test drug dilution there can be added 50 µl of arachidonic acid in MEM to give a 10 µM final concentration and there can be added as well 100 µl of cell suspension to give a final concentration of $1.6 \times 10^5$ cells/mL. The test sample suspensions can be incubated for 1 hour and then centrifuged at 1000 rpm for 10 minutes at 4° C., after which 50 µl aliquots of each test drug sample can be delivered to EIA plates. The EIA can be performed for prostaglandin $E_2$ ($PGE_2$) and the pg/mL concentration of $PGE_2$ can be calculated from the standard line included on each plate. From this data it can be possible to calculate the percent inhibition of COX-2 and the $IC_{50}$ values for the test drug compounds. Repeated investigations of COX-1 and COX-2 inhibition can be conducted over the course of several months. The results are averaged and a single COX-1:COX-2 ratio is calculated.

Whole blood assays for COX-1 and COX-2 are known in the art such as the methods described in C. Brideau, et al., *A Human Whole Blood Assay for Clinical Evaluation of Biochemical Efficacy of Cyclooxygenase Inhibitors, Inflammation Research*, Vol. 45, pp. 68–74 (1996). These methods may be applied with feline, canine or human blood as needed.

In Vivo Assays

Carrageenan Induced Foot Edema in Rats

Male Sprague-Dawley rats (5 weeks old, Charles River Japan) can be fasted overnight. A line can be drawn using a marker above the ankle on the right hind paw and the paw volume (V0) can be measured by water displacement using a plethysmometer (Muromachi). Animals can be given orally either vehicle (0.1% methyl cellulose or 5% Tween 80) or a test compound (2.5 ml per 100 g body weight). One hour later, the animals can then be injected intradermally with λ-carrageenan (0.1 ml of 1% w/v suspension in saline, Zushikagaku) into right hind paw (Winter et al., *Proc. Soc. Exp. Biol. Med.*, 111, 544, 1962; Lombardino et al., *Arzneim. Forsch.*, 25, 1629, 1975) and three hours later, the paw volume (V3) can be measured and the increase in volume (V3−V0) calculated. Since maximum inhibition attainable with classical NSAIDs is 60–70%, $ED_{30}$ values can be calculated.

Gastric Ulceration in Rats

The gastric ulcerogenicity of test compound can be assessed by a modification of the conventional method (Ezer et al., *J. Pharm. Pharmacol.*, 28, 655, 1976; Cashin et al., *J. Pharm. Pharmacol.*, 29, 330–336, 1977). Male Sprague-Dawley rats (5 weeks old, Charles River Japan), fasted overnight, can be given orally either vehicle (0.1% methyl cellulose or 5% Tween 80) or a test compound (1 ml per 100 g body weight). Six hours after, the animals can be sacrificed by cervical dislocation. The stomachs can be removed and inflated with 1% formalin solution (10 ml). Stomachs can be opened by cutting along the greater curvature. From the number of rats that showed at least one gastric ulcer or haemorrhaging erosion (including ecchymosis), the incidence of ulceration can be calculated. Animals did not have access to either food or water during the experiment.

Canine Whole Blood ex vivo Determinations of COX-1 and COX-2 Activity Inhibition The in vivo inhibitory potency of a test compound against COX-1 and COX-2 activity may be evaluated using an ex vivo procedure on canine whole blood. Three canines can be dosed with 5 mg/kg of the test compound administered by oral gavage in 0.5% methylcellulose vehicle and three canines can be untreated. A zero-hour blood sample can be collected from all canines in the study prior to dosing, followed by 2- and 8-hour post-dose blood sample collections. Test tubes can be prepared containing 2 µL of either (A) calcium ionophore A23187 giving a 50 µM final concentration, which stimulates the production of thromboxane $B_2$ ($TXB_2$) for COX-1 activity determination; or of (B) lipopolysaccharide (LPS) to give a 10 µg/mL final concentration, which stimulates the production of prostaglandin $E_2$ ($PGE_2$) for COX-2 activity determination. Test tubes with unstimulated vehicle can be used as controls. A 500 µL sample of blood can be added to each of the above-described test tubes, after which they can be incubated at 37° C. for one hour in the case of the calcium ionophore-containing test tubes and overnight in the case of the LPS-containing test tubes. After incubation, 10 µL of EDTA can be added to give a final concentration of 0.3%, in order to prevent coagulation of the plasma which sometimes occurs after thawing frozen plasma samples. The incubated samples can be centrifuged at 4° C. and the resulting plasma sample of ~200 µL can be collected and stored at −20° C. in polypropylene 96-well plates. In order to determine endpoints for this study, enzyme immunoassay (EIA) kits available from Cayman can be used to measure production of $TXB_2$ and $PGE_2$, utilizing the principle of competitive binding of tracer to antibody and endpoint determination by colorimetry. Plasma samples can be diluted to approximate the range of standard amounts which would be supplied in a diagnostic or research tools kit, i.e., 1/500 for $TXB_2$ and 1/750 for $PGE_2$.

The data set out in Table 1 below show how the percent inhibition of COX-1 and COX-2 activity is calculated based on their zero hour values. The data is expressed as treatment group averages in pg/ml of $TXB_2$ and $PGE_2$ produced per sample. Plasma dilution can be not factored in said data values.

The data in Table 1 show that, in this illustration, at the 5 mg/kg dose there can be significant COX-2 inhibition at both timepoints. The data in Table 1 also show that at the 5 mg/kg dose there can be no significant inhibition of COX-1 activity at the timepoints involved. Accordingly, the data in Table 1 clearly demonstrates that at the 5 mg/kg dosage concentration this compound possesses good COX-2 selectivity.

TABLE 1

| COX-1 ACTIVITY INHIBITION - Group Averages | | | | | |
| --- | --- | --- | --- | --- | --- |
| | $TXB_2$ Pg/mL/Well | | | Percent Inhibition | |
| Hour | 0-hour | 2-hour | 8-hour | 2-hour | 8-hour |
| Untreated | 46 | 45 | 140 | 2% | 0% |
| 5 mg/kg | 41 | 38 | 104 | 7% | 0% |

| COX-2 ACTIVITY INHIBITION - Group Averages | | | | | |
| --- | --- | --- | --- | --- | --- |
| | $PGE_2$ Pg/mL/Well | | | Percent Inhibition | |
| Hour | 0-hour | 2-hour | 8-hour | 2-hour | 8-hour |
| Untreated | 420 | 486 | 501 | 0% | 0% |
| 5 mg/kg | 711 | 165 | 350 | 77% | 51% |

COX inhibition is observed when the measured percent inhibition is greater than that measured for untreated controls. The percent inhibition in the above table is calculated in a straightforward manner in accordance with the following equation:

$$\% \text{ Inhibition (2-hour)} = \frac{(PGE_2 \text{ at } t = 0) - (PGE_2 \text{ at } t = 2)}{(PGE_2 \text{ at } t = 0)}$$

Data Analysis

Statistical program packages, SYSTAT (SYSTAT, INC.) and StatView (Abacus Cencepts, Inc.) for Macintosh can be used. Differences between test compound treated group and control group can be tested for using ANOVA. The $IC_{50}$ (ED30) values can be calculated from the equation for the log-linear regression line of concentration (dose) versus percent inhibition.

Representative compounds prepared in the Working Examples as described hereinafter can be tested by at least one of the methods described above and showed $IC_{50}$ values of 0.001 µM to 25 µM with respect to inhibition of COX-2 in either the canine, feline or human assays.

COX-2 selectivity can be determined by ratio in terms of $IC_{50}$ value of COX-1 inhibition to COX-2 inhibition. In general, it can be said that a compound showing a COX-1/COX-2 inhibition ratio of more than 5 has good COX-2 selectivity. Preferably, compounds of the present invention have a COX-2 selectivity ratio (i.e., COX-1/COX-2) of at least about 5, more preferably of at least about 25. In addition, compounds of the present invention have a COX-2 $IC_{50}$ of less than about 25 µM. By way of comparison, 6-Fluoro-5-methyl-2-oxo-3-(pyrazine-2-carbonyl)-2,3-dihydro-indole-1-carboxylic acid (3,5-dimethyl-phenyl)-amide, a closely related analgesic compound not within the scope of the present invention, has an $IC_{50}$ for COX-2 of greater than about 150 µM, and has an IC50 for COX-1 of greater than about 150 µM, thus having no selectivity for COX-2.

The compounds of the formula I of this invention can be administered via oral, parenteral, anal, buccal or topical routes to mammals (including humans, canines, felines, equines and livestock).

These compounds are most desirably administered to said non-human mammals, e.g. canines, felines, equines or livestock in an amount, expressed as mg per kg of body weight of said member per day, ranging from about 0.01 mg/kg to about 100.0 mg/kg/day, preferably from about 0.5 mg/kg to about 50.0 mg/kg/day, more preferably from about 1 mg/kg to about 10.0 mg/kg/day and most preferably from about 0.5 mg/kg to about 8.0 mg/kg/day.

The compounds of the present invention may be administered alone or in combination with pharmaceutically acceptable carriers or diluents by either of the above routes previously indicated and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging from 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene glycols. Optionally tablets may contain sweetening or flavoring agents to improve the palatability of the tablet. When aqueous suspensions and/or elixirs are desired for oral administration, the active ingredient may also be combined with various sweetening or flavoring agents, coloring matter or dyes and, if so desired, emulsifying and/or suspending agents as well, together with such diluents as water, ethanol, propylene glycol, glycerin and various combinations thereof.

A preferred composition for felines and canines is a flavored tablet with high palatability.

Another preferred composition for felines and canines comprises an ingestible liquid peroral dosage form selected from the group consisting of a solution, suspension, emulsion, inverse emulsion, elixir, extract, tincture and concentrate, optionally to be added to the food of the feline or canine being treated. Any of these liquid dosage forms, when formulated in accordance with methods well known in the art, can either be administered directly to the feline or canine being treated, or may be added to the food of the feline or canine being treated. The concentrate liquid form, on the other hand, is formulated to be added first to a given amount of water, from which an aliquot amount may be withdrawn for administration directly to the feline or canine or addition to the food of the feline or canine.

A preferred composition provides delayed-, sustained- and/or controlled-release of said anti-inflammatory selective COX-2 inhibitor. Such preferred compositions include all such dosage forms which produce ≧80% inhibition of COX-2 isozyme activity and result in a plasma concentration of said inhibitor of at least 3 fold the COX-2 $IC_{50}$ for at least 4 hours; preferably for at least 8 hours; more preferably for at least 12 hours; more preferably still for at least 16 hours; even more preferably still for at least 20 hours; and most preferably for at least 24 hours. Preferably, there is included within the above-described dosage forms those which produce ≧80% inhibition of COX-2 isozyme activity and result in a plasma concentration of said inhibitor of at least 5 fold the COX-2 $IC_{50}$ for at least 4 hours, preferably for at least 8 hours, more preferably for at least 12 hours, still more preferably for at least 20 hours and most preferably for at least 24 hours. More preferably, there is included the above-described dosage forms which produce ≧90% inhibition of COX-2 isozyme activity and result in a plasma concentration of said inhibitor of at least 5 fold the COX-2 $IC_{50}$ for at least 4 hours, preferably for at least 8 hours, more preferably for at least 12 hours, still more preferably for at least 20 hours and most preferably for at least 24 hours.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The compounds of formula I may also be administered in the form of suppositories for rectal or vaginal administration of the active ingredient. These compositions can be prepared by mixing the active ingredient with a suitable non-irritating excipient which is solid at room temperature (for example, 10° C. to 32° C.) but liquid at the rectal temperature and will melt in the rectum or vagina to release the active ingredient. Such materials are polyethylene glycols, cocoa butter, suppository and wax.

For buccal administration, the composition may take the form of tablets or lozenges formulated in conventional manner.

For transdermal administration, transdermal patches prepared in accordance with well known drug delivery technology may be prepared and applied to the skin of a mammal, preferably a human or a canine, to be treated, whereafter the active agent by reason of its formulated solubility characteristics migrates across the epidermis and into the dermal layers of the skin where it is taken up as part of the general circulation, ultimately providing systemic distribution of the active ingredient over a desired, extended period of time. Also included are implants which are placed beneath the epidermal layer of the skin, i.e. between the epidermis and the dermis of the skin of the patient being treated. Such an implant will be formulated in accordance with well known principles and materials commonly used in this delivery technology and may be prepared in such a way as to provide controlled-, sustained- and/or delayed-release of the active ingredient into the systemic circulation of the patient. Such subepidermal (subcuticular) implants provide the same facility of installation and delivery efficiency as transdermal patches, but without the limitation of being subject to degradation, damage or accidental removal as a consequence of being exposed on the top layer of the patient's skin.

EXAMPLES

The following examples contain detailed descriptions of the methods of the preparation of compounds of formula I. These detailed descriptions fall within the scope of the invention and serve to exemplify the above described general synthetic procedures which form part of the invention. These detailed descriptions are presented for illustrative purposes only and are not intended to restrict the scope of the present invention.

The invention is illustrated in the following non-limiting examples in which, unless stated otherwise: all operations were carried out at room or ambient temperature, that is, in the range of 18–25° C.; evaporation of solvent was carried out using a rotary evaporator under reduced pressure with a bath of up to 60° C.; reactions were monitored by thin layer chromatography (TLC) or analytical column liquid chromatography and reaction times are given for illustration only; melting points (m.p.) given are uncorrected (polymorphism may result in different melting points); structure and purity of all isolated compounds were assured by at least one of the following techniques: TLC (Merck silica gel 60 F-254 precoated plates), high performance liquid chromatograpy (HPLC), or mass spectrometry. Flash column chromatography was carried out using Merck silica gel 60 (230–400 mesh ASTM). Low-resolution mass spectral data (API) were obtained on a Fision Platform mass spectrometer. $^1$H NMR data were obtained on a Varian Unity Inova 400 system.

Example 1

Synthesis of 5-Chloro-3-(5-methyl-pyrazine-2-carbonyl)-2-oxo-2,3-dihydro-indole-1-carboxylic acid ethylamide 5-Chloro-3-(5-methyl-pyrazine-2-carbonyl)-2-oxo-2,3-dihydro-indole-1-carboxylic acid ethylamide is prepared in two steps from commercially available 5-chlorooxindole, as outlined in the scheme set forth below.

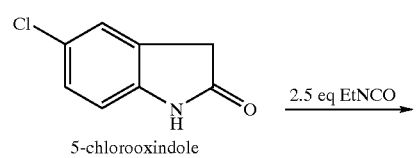

5-chlorooxindole

-continued

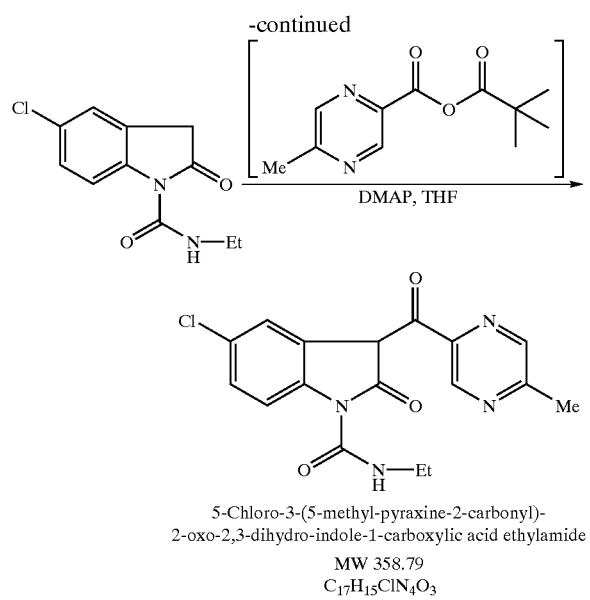

5-Chloro-3-(5-methyl-pyraxine-2-carbonyl)-
2-oxo-2,3-dihydro-indole-1-carboxylic acid ethylamide
MW 358.79
C$_{17}$H$_{15}$ClN$_4$O$_3$ Ethyl isocyanate (71.37 ml, 2.5 eq) was added to a solution of 5-chlorooxindole (60.45 g, 1.0 eq) in 500 ml xylenes. The reaction mixture was heated under reflux for 2 hours (138° C.) and then cooled to room temperature and evaporated to dryness. Isopropyl ether (500 ml) was added to the reaction vessel and the mixture was heated to 60° C. and stirred about 2 hours before cooling overnight in an ice bath to promote crystallization of the product. The white crystalline product was collected by filtration, washed once with isopropyl ether and then dried under vacuum to afford 5-Chloro-2-oxo-2,3-dihydro-indole-1-carboxylic acid ethylamide in 90% yield (78.0 g), mp 121–122° C.

The 5-methyl pyrazine-2-carboxylic acid (3.19 g, 1.1 eq) was added to 50 ml of tetrahydrofuran. Triethylamine (3.7 ml, 1.25 eq) was added and after 5 min of stirring the pivaloyl chloride (3.14 ml, 1.2 eq) was added. The mixture was stirred at room temperature for 1.5 hours and then filtered to remove the triethylamine-hydrochloride salt. 5-Chloro-2-oxo-2,3-dihydro-indole-1-carboxylic acid ethylamide (5.0 g, 1 eq) was added to the filtrate, followed by 2.91 ml of triethylamine (1 eq) and 0.256 g 4-(N,N-dimethylamino)pyridine (0.1 eq). The solution was stirred at room temperature overnight. Then 90 ml of 5% HCl were added and the reaction mixture was stirred for 2.5 hours. The product was collected by filtration and dried under vacuum. The product was stirred in ethyl acetate (90 ml) for 2.5 hours, collected by filtration and dried under vacuum (6.1 g, 81%). It could also be recrystallized from isopropyl ether. The product was then characterized by MS and NMR.

The following compounds summarized in the following Table 2 may be prepared according to the procedure described in the above Example 1 or by the general procedure described below with appropriate starting materials.

General Synthetic Procedure for the Preparation of Examples 2–25

A solution of the appropriate carboxylic acid (1.2 eq) and 1,1'-Carbonyldiimidazole (1.3 eq) in dimethylformamide was allowed to stir for one hour under nitrogen. The reaction vessel was subsequently charged with the appropriate oxindole (1.0 eq), 4-dimethylaminopyridine (2.5 eq) and additional N,N-dimethylformamide (as necessary to facilitate stirring). After 12–20 hours, 1N HCl (5–15 volumes) was added and the solid was collected, rinsed with water and dried. Recrystallization from hot ethanol afforded the desired compounds of examples 2–25, which were then characterized by MS and/or NMR.

TABLE 2

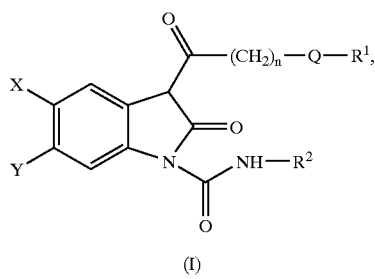

(I)

Q in the

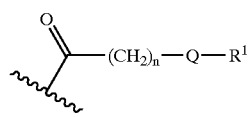

| Ex. # | group | n | R$^1$ | R$^2$ | X | Y | MW | MS (AP-) | $^1$H NMR (δ ppm) |
|---|---|---|---|---|---|---|---|---|---|
| 1 | (pyrazine-2,5-diyl) | 0 | CH$_3$ | —CH$_2$CH$_3$ | Cl | H | 358.79 | 357 | 8.8(d); 8.6(s); 8.08(d); 7.9(s); 7.15(d); 3.2(t); 2.48(s); 1.05(m) |

TABLE 2-continued

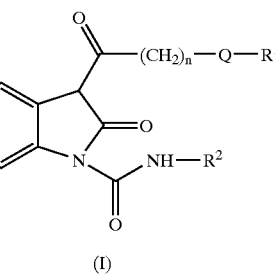

(I)

Q in the

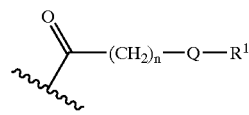

| Ex. # | group | n | R¹ | R² | X | Y | MW | MS (AP-) | ¹H NMR (δ ppm) |
|---|---|---|---|---|---|---|---|---|---|
| 2 | pyrazine | 0 | H | —CH(CH₃)₂ | Cl | H | 358.79 | 357 | 8.8(s); 8.7(s); 8.6(s); 8.04(d); 7.9(d); 7.8(d); 3.8(m); 1.08(d) |
| 3 | pyrazine | 0 | CH₃ | —CH₂CH₂CH₃ | H | Cl | 372.81 | 372 | 8.8(s); 8.7(s); 8.2(s); 7.95(d); 7.24(d); 3.2(m); 2.5(s); 1.5(m); 0.85(t) |
| 4 | pyrazine | 0 | CH₃ | —CH₂CH₂CH₃ | Cl | H | 372.81 | 372 | 8.8(s); 8.7(s); 8.1(d); 7.9(d); 7.2(d). 3.2(m); 2.6(s); 1.5(m); 0.85(t) |
| 5 | pyrazine | 0 | H | —CH₂CH₂CH₃ | F | Cl | 376.78 | 375 | 9.2(m); 8.7(d); 8.6(s); 8.15(d); 7.8(d); 3.2(m); 1.5(q); 0.8(t) |
| 6 | pyrazine | 0 | CH₃ | —CH₂CH₂CH₂CH₃ | H | H | 352.4 | 351 | 8.8(s); 8.7(s); 7.9(d); 7.2(m); 3.2(m); 2.5(s); 1.45(m); 1.3(m); 0.8(t) |
| 7 | pyrazine | 0 | H | —CH₂CH₂CH₃ | Cl | H | 358.79 | 357 | 8.9(m); 8.85(s); 8.7 (d); 8.1(d); 7.9(d); 3.2(m); 1.5(m); 0.85(t) |
| 8 | pyrazine | 0 | H | —CH(CH₃)₂ | F | Cl | 376.78 | 375 | 8.9(d); 8.7(s); 8.66(s); 8.62(s); 8.14(d); 7.8(d); 3.8(m); 1.08(d) |
| 9 | pyridine | 0 | H | —CH(CH₃)₂ | Cl | H | 357.8 | 356 | 9.3(d); 9.0(s); 8.8(d); 8.6(d); 8.0(m); 6.8(d); 3.8(m); 1.08(d) |
| 10 | pyrazine | 0 | CH₃ | —CH₂CH₂CH₃ | H | H | 338.37 | 337 | 8.8(s); 8.7(s); 8.15(d); 7.9(d); 7.2(m); 3.2(m); 2.5(s); 1.5(m); 0.8(t) |
| 11 | pyrazine | 0 | H | —C(CH₃)₃ | Cl | H | 372.81 | 371 | 8.8(d); 8.7(d); 8.06(d); 7.9(s); 7.1(d); 1.02(d) |

TABLE 2-continued

| Ex. # | Q in the group | n | R¹ | R² | X | Y | MW | MS (AP-) | ¹H NMR (δ ppm) |
|---|---|---|---|---|---|---|---|---|---|
| 12 | pyrazine (2,5) | 0 | CH₃ | —CH(CH₃)₂ | F | Cl | 390.81 | 391 | 8.9(d); 8.7(s); 8.6 (s); 8.2(d); 7.8(d); 3.9(m); 2.5(s); 1.1(d) |
| 13 | pyrazine (2,5) | 0 | CH₃ | —CH₂CH₂CH₂CH₃ | Cl | H | 386.84 | 385 | 8.9(m); 8.8(d); 8.7(d); 8.1(d); 7.9(d); 7.15(dd); 3.2(m); 2.6(s); 1.45(m); 1.3(m); 0.9(t) |
| 14 | pyrazine (2,5) | 0 | CH₃ | —C(CH₃)₃ | Cl | H | 386.84 | 385 | 8.8(t); 8.7(d); 8.1(dd); 7.9(d); 7.2(dd); 3.2(s); 2.6(s); 1.3(s) |
| 15 | pyrazine (2,5) | 0 | H | —CH₂CH₂CH₃ | H | Cl | 358.79 | 358 | 8.9(s); 8.8(m); 8.7(s); 8.2(s); 7.9(d); 7.2(dd) 3.2(m); 2.5(m); 0.8(t) |
| 16 | pyridine (2,5) | 0 | H | —C(CH₃)₃ | Cl | H | 371.83 | 370 | 9.4(s); 9.02(d); 8.8(d); 8.6(d); 8.0(m); 6.8(d); 1.3(s) |
| 17 | pyrazine (2,5) | 0 | CH₃ | —CH(CH₃)₂ | Cl | H | 372.81 | 371 | 8.8(s); 8.6(s); 8.1(d); 0.79(d); 7.18(dd); 3.9(m); 2.6(s); 1.1(d) |
| 18 | pyridine (3,5) | 0 | Br | —CH(CH₃)₂ | Cl | H | 436.7 | 436 | 9.06(d); 8.8(d); 8.7(d); 8.2(dd); 8.09(d); 7.9(d); 7.059(dd); 3.9 (m); 1.14(d) |
| 19 | pyridine (3,5) | 0 | Br | —CH₂CH₂CH₃ | H | H | 402.25 | 402 | 8.9(m); 8.8(d); 8.74(d); 8.28(t); 8.14(m); 7.96(m); 7.1(m); 3.2(m); 1.5(m); 0.86(t) |

TABLE 2-continued

Structure (I):

X, Y substituents on indoline-2,3-dione core with N-C(O)-NH-R² and 3-C(O)-(CH₂)ₙ-Q-R¹ substituents.

| Ex. # | Q group | n | R¹ | R² | X | Y | MW | MS (AP-) | ¹H NMR (δ ppm) |
|---|---|---|---|---|---|---|---|---|---|
| 20 | pyrazine-2,5-diyl | 0 | H | —CH₂CH₃ | Cl | H | 344.76 | 343 | 8.8(s); 8.73(m); 7.68(m); 8.05(d); 7.9(d); 7.1(dd); 3.2(m); 1.02(t) |
| 21 | pyridine-3,5-diyl | 0 | Br | —CH(CH₃)₂ | H | H | 402.25 | 402 | 8.8(d); 8.7(d); 8.3(t); 8.14(d); 7.9(d); 7.2(m); 3.9(m); 3.2(s); 2.5(m); 1.2(d) |
| 22 | pyridine-3,5-diyl | 0 | Br | —CH₂CH₂CH₃ | Cl | H | 436.7 | 435 | 9.01(m); 8.8(d); 8.7(d); 8.3(t); 8.1(d); 7.9(d); 7.1(dd); 3.2(m); 1.5(q); 0.8(t) |
| 23 | pyrazine-2,5-diyl | 0 | H | cyclohexyl | Cl | H | 398.85 | 397 | 8.85(s); 8.8(d); 8.7(d); 8.05(d); 7.9(s); 7.1(s); 3.6(m); 1.8(m); 1.6(m); 1.5(m); 1.2(m) |
| 24 | pyrazine-2,5-diyl | 0 | CH₃ | cyclohexyl | Cl | H | 412.88 | 412 | 8.8(s); 8.7(s); 8.1(d); 7.98(s); 7.2(d); 3.65(m); 2.6(s); 1.9(m); 1.7(m); 1.57(m); 1.3(m) |
| 25 | pyridine-2,5-diyl | 0 | Cl | —CH₂CH₃ | H | Cl | 378.22 | 376 | 8.9(m); 8.8(s); 8.2(s); 8.1(dd); 7.9(d); 7.6(d); 7.2(dd); 3.25(m); 1.09(t) |

Referring to Table 2, Ex.#. refers to Example number; MW refers to molecular weight in gram/mole; MS (AP-) refers to mass spectra; and Q in the

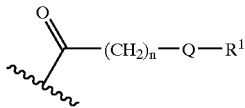

group refers to the orientation of the group —Q— in such group from left to right.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula I:

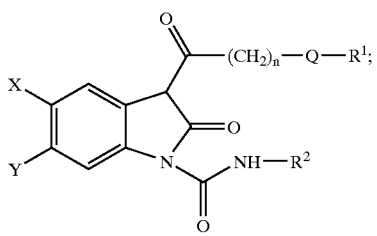

or a pharmaceutically-acceptable salt thereof;
wherein X is hydrogen, halogen, $-NO_2$, $(C_1-C_6)$alkyl, $-CF_3$, $(C_3-C_8)$cycloalkyl, $(C_1-C_6)$alkyl-O—, $(C_1-C_6)$alkyl-S—, $(C_1-C_6)$alkyl-SO—, $(C_1-C_6)$alkyl-$SO_2$—; $(C_1-C_6)$alkyl-(C=O)—, $(C_6-C_{10})$aryl-(C=O)—, $(C_1-C_{10})$heteroaryl-(C=O)—, $(C_1-C_{10})$heterocyclyl-(C=O)—, $(C_1-C_6)$alkyl-NH—(C=O)—, $(C_6-C_{10})$aryl-NH—(C=O)—, or $[(C_1-C_6)$alkyl]$_2$-N—$SO_2$—;

Y is hydrogen, halogen, $-NO_2$, $(C_1-C_6)$alkyl, $-CF_3$, $(C_3-C_8)$cycloalkyl, $(C_1-C_6)$alkyl-O—, $(C_1-C_6)$alkyl-S—, $(C_1-C_6)$alkyl-SO—, $(C_1-C_6)$alkyl-$SO_2$—; $(C_1-C_6)$alkyl-(C=O)—, $(C_6-C_{10})$aryl-(C=O)—, $(C_1-C_{10})$heteroaryl-(C=O)—, $(C_1-C_{10})$heterocyclyl-(C=O)—, $(C_1-C_6)$alkyl-NH—(C=O)—, $(C_6-C_{10})$aryl-NH—(C=O)—, or $[(C_1-C_6)$alkyl]$_2$-N—$SO_2$—;

n is 0, 1 or 2;

Q is a 6-membered heterocyclic divalent radical of pyran, piperidine, 1,4-dioxane, morpholine, dithiane, thiomorpholine, pyridazine, piperazine, pyridine, pyrimidine, pyrazine, 1,3,5-triazine, or 1,3,5-trithiane;

$R^1$ is hydrogen, halogen or $(C_1-C_6)$alkyl; and $R^2$ is $(C_1-C_6)$alkyl or $(C_3-C_8)$cycloalkyl.

2. A compound according to claim 1 wherein Q is a 6-membered heterocyclic divalent radical of pyridine and pyrazine.

3. A compound according to claim 1 wherein Q is 3-pyridinyl or 2-pyrazinyl, and $R^2$ is $(C_1-C_6)$alkyl.

4. A compound according to claim 1 wherein $R^1$ is hydrogen, halogen or $(C_1-C_6)$alkyl, and $R^2$ is $(C_1-C_6)$alkyl.

5. A compound according to claim 1 wherein $R^2$ is ethyl, propyl, or isopropyl.

6. A compound according to claim 1 wherein X is hydrogen, fluoro or chloro.

7. A compound according to claim 1 wherein Y is hydrogen, fluoro or chloro.

8. A compound according to claim 1 wherein X is chloro and Y is hydrogen.

9. A compound according to claim 1 wherein said compound is selected from the group consisting of:
5-Chloro-3-(5-methyl-pyrazine-2-carbonyl)-2-oxo-2,3-dihydro-indole-1-carboxylic acid ethylamide;
5-Chloro-2-oxo-3-(pyrazine-2-carbonyl)-2,3-dihydro-indole-1-carboxylic acid isopropylamide;
6-Chloro-3-(5-methyl-pyrazine-2-carbonyl)-2-oxo-2,3-dihydro-indole-1-carboxylic acid propylamide;
5-Chloro-3-(5-methyl-pyrazine-2-carbonyl)-2-oxo-2,3-dihydro-indole-1-carboxylic acid proprylamide;
6-Chloro-5-fluoro-2-oxo-3-(pyrazine-2-carbonyl)-2,3-dihydro-indole-1-carboxylic acid propylamide;
3-(5-Methyl-pyrazine-2-carbonyl)-2-oxo-2,3-dihydro-indole-1-carboxylic acid butylamide;
5-Chloro-2-oxo-3-(pyrazine-2-carbonyl)-2,3-dihydro-indole-1-carboxylic acid propylamide;
6-Chloro-5-fluoro-2-oxo-3-(pyrazine-2-carbonyl)-2,3-dihydro-indole-1-carboxylic acid isopropylamide;
5-Chloro-2-oxo-3-(pyridine-3-carbonyl)-2,3-dihydro-indole-1-carboxylic acid isopropylamide;
3-(5-Methyl-pyrazine-2-carbonyl)-2-oxo-2,3-dihydro-indole-1-carboxylic acid propylamide;
5-Chloro-2-oxo-3-(pyrazine-2-carbonyl)-2,3-dihydro-indole-1-carboxylic acid tert-butylamide;
6-Chloro-5-fluoro-3-(5-methyl-pyrazine-2-carbonyl)-2-oxo-2,3-dihydro-indole-1-carboxylic acid isopropylamide;
5-Chloro-3-(5-methyl-pyrazine-2-carbonyl)-2-oxo-2,3-dihydro-indole-1-carboxylic acid butylamide;
5-Chloro-3-(5-methyl-pyrazine-2-carbonyl)-2-oxo-2,3-dihydro-indole-1-carboxylic acid tert-butylamide;
6-Chloro-2-oxo-3-(pyrazine-2-carbonyl)-2,3-dihydro-indole-1-carboxylic acid propylamide;
5-Chloro-2-oxo-3-(pyridine-3-carbonyl)-2,3-dihydro-indole-1-carboxylic acid tert-butylamide;
5-Chloro-3-(5-methyl-pyrazine-2-carbonyl)-2-oxo-2,3-dihydro-indole-1-carboxylic acid isopropylamide;
3-(5-Bromo-pyridine-3-carbonyl)-5-chloro-2-oxo-2,3-dihydro-indole-1-carboxylic acid isopropylamide;
3-(5-Bromo-pyridine-3-carbonyl)-2-oxo-2,3-dihydro-indole-1-carboxylic acid propylamide;
5-Chloro-2-oxo-3-(pyrazine-2-carbonyl)-2,3-dihydro-indole-1-carboxylic acid ethylamide;
3-(5-Bromo-pyridine-3-carbonyl)-2-oxo-2,3-dihydro-indole-1-carboxylic acid isopropylamide;
3-(5-Bromo-pyridine-3-carbonyl)-5-chloro-2-oxo-2,3-dihydro-indole-1-carboxylic acid propylamide;
5-Chloro-2-oxo-3-(pyrazine-2-carbonyl)-2,3-dihydro-indole-1-carboxylic acid cyclohexylamide;
5-Chloro-3-(5-methyl-pyrazine-2-carbonyl)-2-oxo-2,3-dihydro-indole-1-carboxylic acid cyclohexylamide; and
6-Chloro-3-(6-chloro-pyridine-3-carbonyl)-2-oxo-2,3-dihydro-indole-1-carboxylic acid ethylamide;
or a pharmaceutically-acceptable salt thereof.

10. A compound according to claim 1 wherein said compound is selected from the group consisting of:
5-Chloro-3-(5-methyl-pyrazine-2-carbonyl)-2-oxo-2,3-dihydro-indole-1-carboxylic acid ethylamide;
5-Chloro-2-oxo-3-(pyrazine-2-carbonyl)-2,3-dihydro-indole-1-carboxylic acid isopropylamide;

6-Chloro-3-(5-methyl-pyrazine-2-carbonyl)-2-oxo-2,3-dihydro-indole-1-carboxylic acid propylamide;

5-Chloro-3-(5-methyl-pyrazine-2-carbonyl)-2-oxo-2,3-dihydro-indole-1-carboxylic acid propylamide;

6-Chloro-5-fluoro-2-oxo-3-(pyrazine-2-carbonyl)-2,3-dihydro-indole-1-carboxylic acid propylamide;

3-(5-Methyl-pyrazine-2-carbonyl)-2-oxo-2,3-dihydro-indole-1-carboxylic acid butylamide;

5-Chloro-2-oxo-3-(pyrazine-2-carbonyl)-2,3-dihydro-indole-1-carboxylic acid propylamide;

6-Chloro-5-fluoro-2-oxo-3-(pyrazine-2-carbonyl)-2,3-dihydro-indole-1-carboxylic acid isopropylamide;

5-Chloro-2-oxo-3-(pyridine-3-carbonyl)-2,3-dihydro-indole-1-carboxylic acid isopropylamide;

3-(5-Methyl-pyrazine-2-carbonyl)-2-oxo-2,3-dihydro-indole-1-carboxylic acid propylamide; and 5-Chloro-2-oxo-3-(pyrazine-2-carbonyl)-2,3-dihydro-indole-1-carboxylic acid tert-butylamide;

or a pharmaceutically-acceptable salt thereof.

11. A compound according to claim 1 wherein said compound is selected from the group consisting of:

5-Chloro-3-(5-methyl-pyrazine-2-carbonyl)-2-oxo-2,3-dihydro-indole-1-carboxylic acid ethylamide;

6-Chloro-3-(5-methyl-pyrazine-2-carbonyl)-2-oxo-2,3-dihydro-indole-1-carboxylic acid propylamide;

6-Chloro-5-fluoro-2-oxo-3-(pyrazine-2-carbonyl)-2,3-dihydro-indole-1-carboxylic acid propylamide;

3-(5-Methyl-pyrazine-2-carbonyl)-2-oxo-2,3-dihydro-indole-1-carboxylic acid butylamide;

5-Chloro-2-oxo-3-(pyrazine-2-carbonyl)-2,3-dihydro-indole-1-carboxylic acid propylamide;

6-Chloro-5-fluoro-2-oxo-3-(pyrazine-2-carbonyl)-2,3-dihydro-indole-1-carboxylic acid isopropylamide;

5-Chloro-2-oxo-3-(pyridine-3-carbonyl)-2,3-dihydro-indole-1-carboxylic acid isopropylamide; and 3-(5-Methyl-pyrazine-2-carbonyl)-2-oxo-2,3-dihydro-indole-1-carboxylic acid propylamide;

or a pharmaceutically-acceptable salt thereof.

12. A compound according to claim 1 wherein said compound is selected from the group consisting of:

5-Chloro-3-(5-methyl-pyrazine-2-carbonyl)-2-oxo-2,3-dihydro-indole-1-carboxylic acid ethylamide;

6-Chloro-3-(5-methyl-pyrazine-2-carbonyl)-2-oxo-2,3-dihydro-indole-1-carboxylic acid propylamide;

6-Chloro-5-fluoro-2-oxo-3-(pyrazine-2-carbonyl)-2,3-dihydro-indole-1-carboxylic acid propylamide;

5-Chloro-2-oxo-3-(pyrazine-2-carbonyl)-2,3-dihydro-indole-1-carboxylic acid propylamide; and 3-(5-Methyl-pyrazine-2-carbonyl)-2-oxo-2,3-dihydro-indole-1-carboxylic acid propylamide;

or pharmaceutically-acceptable salts thereof.

13. A compound according to claim 1 wherein said compound is 5-chloro-3-(5-methyl-pyrazine-2-carbonyl)-2-oxo-2,3-dihydro-indole-1-carboxylic acid ethylamide.

14. A method of inhibiting cyclooxygenase-2 comprising administering to a mammal in need thereof an effective amount of a compound of formula I:

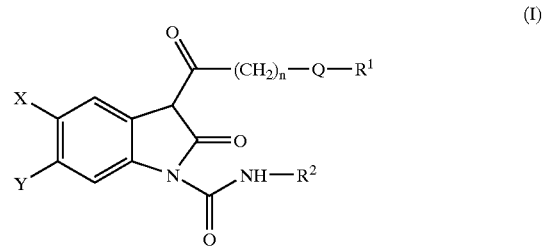

or a pharmaceutically-acceptable salt thereof;

wherein X is hydrogen, halogen, —NO$_2$, (C$_1$–C$_6$)alkyl, —CF$_3$, (C$_3$–C$_8$)cycloalkyl, (C$_1$–C$_6$)alkyl-O—, (C$_1$–C$_6$)alkyl-S—, (C$_1$–C$_6$)alkyl-SO—, (C$_1$–C$_6$)alkyl-SO$_2$—; (C$_1$–C$_6$)alkyl-(C=O)—, (C$_6$–C$_{10}$)aryl-(C=O)—, (C$_1$–C$_{10}$)heteroaryl-(C=O)—, (C$_1$–C$_{10}$)heterocyclyl-(C=O)—, (C$_1$–C$_6$)alkyl-NH—(C=O)—, (C$_6$–C$_{10}$)aryl-NH—(C=O)—, or [(C$_1$–C$_6$)alkyl]$_2$-N—SO$_2$—;

Y is hydrogen, halogen, —NO$_2$, (C$_1$–C$_6$)alkyl, —CF$_3$, (C$_3$–C$_8$)cycloalkyl, (C$_1$–C$_6$)alkyl-O—, (C$_1$–C$_6$)alkyl-S—, (C$_1$–C$_6$)alkyl-SO—, (C$_1$–C$_6$)alkyl-SO$_2$—; (C$_1$–C$_6$)alkyl-(C=O)—, (C$_6$–C$_{10}$)aryl-(C=O)—, (C$_1$–C$_{10}$)heteroaryl-(C=O)—, (C$_1$–C$_{10}$)heterocyclyl-(C=O)—, (C$_1$–C$_6$)alkyl-NH—(C=O)—, (C$_6$–C$_{10}$)aryl-NH—(C=O)—, or [(C$_1$–C$_6$)alkyl]$_2$-N—SO$_2$—;

n is 0, 1 or 2;

Q is a 6-membered heterocyclic divalent radical of pyran, piperidine, 1,4-dioxane, morpholine, dithiane, thiomorpholine, pyridazine, piperazine, pyridine, pyrimidine, pyrazine, 1,3,5-triazine, or 1,3,5-trithiane;

R$^1$ is hydrogen, halogen or (C$_1$–C$_6$)alkyl; and

R$^2$ is (C$_1$–C$_6$)alkyl or (C$_3$–C$_8$)cycloalkyl.

15. A method according to claim 14 wherein said compound is 5-chloro-3-(5-methyl-pyrazine-2-carbonyl-2-oxo-2,3-dihydro-indole-1-carboxylic acid ethylamide.

16. A method according to claim 14 wherein the mammal is a human.

17. A method according to claim 14 wherein the mammal is a feline.

18. A method according to claim 14 wherein the mammal is a canine.

19. A method according to claim 14 wherein the compound is administered in an amount of from about 0.5 mg/kg body weight/day to about 50 mg/kg body weight/day.

20. A method according to claim 14 wherein the compound is administered in an amount of from about 1 mg/kg body weight/day to about 10 mg/kg body weight/day.

21. A method of treating a condition selected from the group consisting of arthritis, fever, common cold, dysmenorrhea, menstrual cramps, inflammatory bowel disease, Crohn's disease, emphysema, asthma, bronchitis, chronic obstructive pulmonary disease, organ transplant toxicity, cachexia, allergic reactions, allergic contact hypersensitivity, peptic ulcers, gastritis, regional enteritis, ulcerative colitis, diverticulitis, recurrent gastrointestinal lesion, gastrointestinal bleeding, anemia, synovitis, gout, ankylosing spondylitis, periodontal disease, epidermolysis bullosa, osteoporosis, loosening of artificial joint implants, atherosclerosis, aortic aneurysm, periarteritis nodosa, congestive heart failure, myocardial infarction, cerebral ischemia, head trauma, spinal cord injury, neuralgia, migraine, depression, peripheral neuropathy, pain, gingivitis, cerebral amyloid angiopathy, amyotrophic lateral sclerosis, multiple sclerosis, ocular angiogenesis, corneal injury, macular degeneration, conjunctivitis, abnormal wound healing, muscle or joint sprains or strains, tendonitis, polymyositis, myositis, bursitis, burns, diabetes, corneal scarring, scleritis, sepsis, premature labor, hypoprothrombinemia, hemophilia, thyroiditis, sarcoidosis, Behcet's syndrome, Rickettsial infections, and Protozoan diseases in a mammal, which comprises administering to said mammalian subject an inflammatory disease treating amount of a compound of formula I:

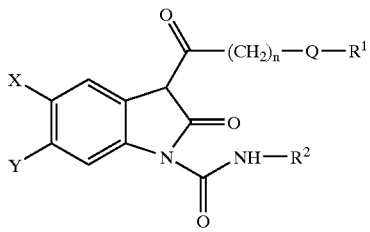
(I)

or a pharmaceutically-acceptable salt thereof;

wherein X is hydrogen, halogen, —$NO_2$, ($C_1$-$C_6$)alkyl, —$CF_3$, ($C_3$-$C_8$)cycloalkyl, ($C_1$-$C_6$)alkyl-O—, ($C_1$-$C_6$)alkyl-S—, ($C_1$-$C_6$)alkyl-SO—, ($C_1$-$C_6$)alkyl-$SO_2$—; ($C_1$-$C_6$)alkyl-(C=O)—, ($C_6$-$C_{10}$)aryl-(C=O)—, ($C_1$-$C_{10}$)heteroaryl-(C=O)—, ($C_1$-$C_{10}$)heterocyclyl-(C=O)—, ($C_1$-$C_6$)alkyl-NH—(C=O)—, ($C_6$-$C_{10}$)aryl-NH—(C=O)—, or [($C_1$-$C_6$)alkyl]$_2$-N—$SO_2$—;

Y is hydrogen, halogen, —$NO_2$, ($C_1$-$C_6$)alkyl, —$CF_3$, ($C_3$-$C_8$)cycloalkyl, ($C_1$-$C_6$)alkyl-O—, ($C_1$-$C_6$)alkyl-S—, ($C_1$-$C_6$)alkyl-SO—, ($C_1$-$C_6$)alkyl-$SO_2$—; ($C_1$-$C_6$)alkyl-(C=O)—, ($C_6$-$C_{10}$)aryl-(C=O)—, ($C_1$-$C_{10}$)heteroaryl-(C=O)—, ($C_1$-$C_{10}$)heterocyclyl-(C=O)—, ($C_1$-$C_8$)alkyl-NH—(C=O)—, ($C_6$-$C_{10}$)aryl-NH—(C=O)—, or [($C_1$-$C_6$)alkyl]$_2$-N—$SO_2$—;

n is 0, 1 or 2;

Q is a 6-membered heterocyclic divalent radical of pyran, piperidine, 1,4-dioxane, morpholine, dithiane, thiomorpholine, pyridazine, piperazine, pyridine, pyrimidine, pyrazine, 1,3,5-triazine, or 1,3,5-trithiane;

$R^1$ is hydrogen, halogen or ($C_1$-$C_6$)alkyl; and $R^2$ is ($C_1$-$C_6$)alkyl or ($C_3$-$C_8$)cycloalkyl.

22. A pharmaceutical composition, which comprises a pharmaceutically-acceptable carrier and an effective analgesic response eliciting or inflammatory disease treating amount of a compound of formula I:

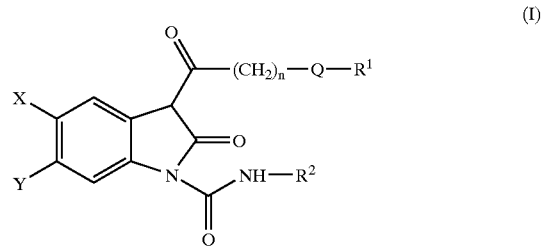
(I)

or a pharmaceutically-acceptable salt thereof;

wherein X is hydrogen, halogen, —$NO_2$, ($C_1$-$C_6$)alkyl, —$CF_3$, ($C_3$-$C_8$)cycloalkyl, ($C_1$-$C_6$)alkyl-O—, ($C_1$-$C_6$)alkyl-S—, ($C_1$-$C_6$)alkyl-SO—, ($C_1$-$C_6$)alkyl-$SO_2$—; ($C_1$-$C_6$)alkyl-(C=O)—, ($C_6$-$C_{10}$)aryl-(C=O)—, ($C_1$-$C_{10}$)heteroaryl-(C=O)—, ($C_1$-$C_{10}$)heterocyclyl-(C=O)—, ($C_1$-$C_6$)alkyl-NH—(C=O)—, ($C_6$-$C_{10}$)aryl-NH—(C=O)—, or [($C_1$-$C_6$)alkyl]$_2$-N—$SO_2$—;

Y is hydrogen, halogen, —$NO_2$, ($C_1$-$C_6$)alkyl, —$CF_3$, ($C_3$-$C_8$)cycloalkyl, ($C_1$-$C_6$)alkyl-O—, ($C_1$-$C_6$)alkyl-S—, ($C_1$-$C_6$)alkyl-SO—; ($C_1$-$C_6$)alkyl-$SO_2$—; ($C_1$-$C_6$)alkyl-(C=O)—, ($C_6$-$C_{10}$)aryl-(C=O)—, ($C_1$-$C_{10}$)heteroaryl-(C=O)—, ($C_1$-$C_{10}$)heterocyclyl-(C=O)—, ($C_1$-$C_6$)alkyl-NH—(C=O)—, ($C_6$-$C_{10}$)aryl-NH—(C=O)—, or [($C_1$-$C_6$)alkyl]$_2$-N—$SO_2$—;

n is 0, 1 or 2;

Q is a 6-membered heterocyclic divalent radical of pyran, piperidine, 1,4-dioxane, morpholine, dithiane, thiomorpholine, pyridazine, piperazine, pyridine, pyrimidine, pyrazine, 1,3,5-triazine, and 1,3,5-trithiane;

$R^1$ is hydrogen, halogen or ($C_1$-$C_6$)alkyl; and $R^2$ is ($C_1$-$C_6$)alkyl or ($C_3$-$C_8$)cycloalkyl.

23. A pharmaceutical composition according to claim 22 further comprising at least one additional therapeutic agent for the treatment of osteoarthritis.

24. The composition according to claim 23 wherein the additional therapeutic agent for the treatment of osteoarthritis is selected from the group consisting of: piroxicam, diclofenac, propionic acids such as carprofen, naproxen, flurbiprofen, fenoprofen, ketoprofen, ibuprofen, mefenamic acid, indomethacin, sulindac, apazone, phenylbutazone, aspirin, celecoxib and rofecoxib, corticosteroids, hyalgan and synvisc.

25. A pharmaceutical composition according to claim 22 further comprising at least one of the chondroprotective nutraceuticals for joint treatment selected from the group consisting of: polysulfated glycosaminoglycan (PSGAG), glucosamine, choridroitin sulfate (CS), hyaluronic acid (HA), and pentosan polysulfate (PPS).

* * * * *